United States Patent
Tokailin et al.

(10) Patent No.: US 7,501,189 B2
(45) Date of Patent: Mar. 10, 2009

(54) WHITE ORGANIC ELECTROLUMINESCENT DEVICE

(75) Inventors: Hiroshi Tokailin, Sodegaura (JP);
Hitoshi Kuma, Sodegaura (JP);
Mineyuki Kubota, Sodegaura (JP);
Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/254,852

(22) Filed: Oct. 21, 2005

(65) Prior Publication Data

US 2006/0127698 A1    Jun. 15, 2006

Related U.S. Application Data

(63) Continuation of application No. PCT/JP2005/009244, filed on May 20, 2005.

(30) Foreign Application Priority Data

May 27, 2004   (JP)   ............... 2004-158285

(51) Int. Cl.
*H01L 51/54* (2006.01)
(52) U.S. Cl. ............ 428/690; 428/917; 313/504; 313/506
(58) Field of Classification Search ........ 428/690, 428/917, 212; 313/504, 506; 257/102, E51.051
See application file for complete search history.

(56) References Cited

U.S. PATENT DOCUMENTS

| | | | | |
|---|---|---|---|---|
| 5,405,709 | A | 4/1995 | Littman et al. | 428/690 |
| 6,632,543 | B1 * | 10/2003 | Kawamura | 428/690 |
| 6,803,120 | B2 * | 10/2004 | Fukuoka et al. | 428/690 |
| 6,866,947 | B1 * | 3/2005 | Fukuoka et al. | 428/690 |

(Continued)

FOREIGN PATENT DOCUMENTS

EP    1 414 081    4/2004

(Continued)

OTHER PUBLICATIONS

Kido, J. et al, "Multilayer White Light-Emitting Organic Electroluminescent Device," Science, vol. 267, Mar. 3, 1995, pp. 1332-1333.

(Continued)

*Primary Examiner*—Dawn Garrett
(74) *Attorney, Agent, or Firm*—Steptoe & Johnson LLP

(57) ABSTRACT

A white organic electroluminescent device (1) including an emitting layer (5, 6 and 7) interposed between an anode (2) and a cathode (9), the emitting layer (5, 6 and 7) emitting blue light, green light and red light, the emitting layer (6) containing a green dopant that is an aromatic amine compound represented by formula (1),

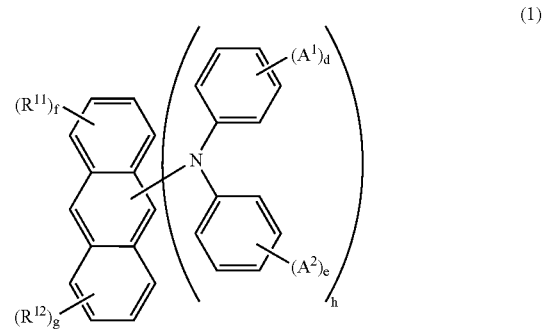

(1)

wherein $A^1$, $A^2$ and $R^{12}$ are a hydrogen atom, an alkyl group, an aryl group, a cycloalkyl group, an alkoxy group, an aryloxy group, an arylamino group, an alkylamino group or a halogen atom; d and e are independently 1 to 5; h is 1 to 9; $R^{11}$ is a secondary or tertiary alkyl or cycloalkyl group; f is 1 to 9; g is 0 to 8 and f+g+h is 2 to 10.

9 Claims, 2 Drawing Sheets

U.S. PATENT DOCUMENTS

| | | | |
|---|---|---|---|
| 2002/0168544 A1* | 11/2002 | Fukuoka et al. | 428/690 |
| 2004/0124766 A1* | 7/2004 | Nakagawa et al. | 313/504 |
| 2005/0019606 A1 | 1/2005 | Fukuoka et al. | 428/690 |
| 2005/0064233 A1* | 3/2005 | Matsuura et al. | 428/690 |
| 2005/0129982 A1 | 6/2005 | Fukuoka et al. | 428/690 |
| 2005/0153163 A1* | 7/2005 | Klubek et al. | 428/690 |

FOREIGN PATENT DOCUMENTS

| | | | |
|---|---|---|---|
| JP | 07-142169 | | 6/1995 |
| JP | 10-003990 | | 1/1998 |
| JP | 2000-068057 | | 3/2000 |
| JP | 2003-086380 | | 3/2003 |
| JP | 2003-187978 | | 7/2003 |
| JP | 2003-229273 | * | 8/2003 |
| JP | 2004-006165 | | 1/2004 |
| JP | 2004-171828 | | 6/2004 |
| JP | 2004-327432 | | 11/2004 |
| WO | WO 2004/018588 | | 3/2004 |
| WO | WO 2004/092111 | | 10/2004 |

OTHER PUBLICATIONS

Deshpande, R.S. et al, "White-light-emitting organic electroluminescent devices based on interlay sequential energy transfer", Applied Physics Letters, vol. 75, No. 7, Aug. 16, 1999, p. 888-890.

* cited by examiner

WHITE ORGANIC ELECTROLUMINESCENT DEVICE

TECHNICAL FIELD

The invention relates to a white organic electroluminescent device.

BACKGROUND ART

An organic electroluminescent device (referred to as "organic EL device" hereinafter) has characteristics of low voltage, high brightness and large viewing angle, and it is expected that a display (organic EL display) having the above organic EL device will be developed to a broad range of uses.

Features of such an organic EL device include the feature that, in principle, hues of blue to red can be obtained as required.

Above all, a white organic EL device can be used directly as a white light source, so that it is expected to be used in the fields of thin film light source backlights for LCD, illumination lamp sources for use in a vehicle or an office, full-color displays such as TV, etc., and the like.

For establishing its use for illumination lamp sources or full-color displays, there is required a white organic EL device having high efficiency and high lifetime. In particular, when the use in displays is considered, there is further required a three-band white organic EL device that has an emission peak in each of wavelength regions of three primary colors of light in addition to the above performances.

As a white organic EL device, for example, there is disclosed an organic EL device having a blue emitting layer adjacent to a hole transporting layer and having, next thereto, a green emitting layer having a region containing a red fluorescent layer (see Patent Document 1).

Further, there is disclosed a white organic EL device that has three types of emitting layers having different carrier transport characteristics for emitting blue light, green light and red light (see non-Patent Document 1).

Further, there is also disclosed a white organic EL device containing emitting layers for emitting blue light in a broad range and red light in a broad range upon electron-hole recombination (see Patent Document 2).

Further, there is also disclosed a white organic EL device containing layers for emitting light in red, blue and green, which layers are isolated with hole-barrier layers (see non-Patent Document 2).

In these devices, however, it is required to control the concentration of a dopant contained in a trace amount, and it is difficult to control the same in a large-scale production process.

Further, there is disclosed a white organic EL device having an emitting layer comprised of three layers, a blue emitting layer, a green emitting layer and a red emitting layer which are stacked in this order from an anode, the blue emitting layer being constituted by incorporating a blue fluorescer into a blue emitting material, the green emitting layer being constituted by incorporating a green fluorescer into a blue or green emitting material, the red emitting layer being constituted by incorporating a red fluorescer into a blue emitting material (see Patent Document 3).

However, the efficiency of this device at a brightness of 200 cd/m$^2$ is as insufficient as 3.7 to 3.9 lm/W.

Further, there is also disclosed a three-band white organic EL device in which a region on the side of a hole transporting layer adjacent to a blue emitting layer is doped with a yellow fluorescer and a region on the side of an electron transporting layer adjacent to the blue emitting layer is doped with a green fluorescer (see Patent Document 4).

However, the efficiency of this device is also as insufficient as 4-5 cd/A.

Further, there is also disclosed a technique of suppressing a change in hue of emitted light on the basis of a driving current in a device having an emitting layer comprised of a red emitting layer, a blue emitting layer and a green emitting layer which are stacked in this order from the anode side, the blue emitting layer as an intermediate layer being doped with an auxiliary dopant that exhibits red light fluorescence (see Patent Document 5).

While a change in hue of emitted light may be suppressed by this technique, nothing is disclosed with regard to the luminous efficiency of a white light device, so that the performance of the device is specifically unclear. Further, white light can be obtained only when the doping concentration of red fluorescer in the blue emitting layer is controlled to be a very small amount, and it is difficult to secure the reproducibility, etc., of making the device.

On the other hand, there is developed a white organic EL device using an unsymmetrical anthracene compound as a host material in an emitting layer (see Patent Document 6).

Further, there is developed an organic EL device using an aromatic amine derivative having an anthracene skeleton as a green dopant for forming a green emitting layer (see Patent Documents 7 and 8).

[Patent Document 1] JP-A-7-142169

[Patent Document 2] U.S. Pat. No. 5,405,709

[Patent Document 3] JP-A-10-3990

[Patent Document 4] JP-A-2003-86380

[Patent Document 5] JP-A-2004-6165

[Patent Document 6] Japanese Patent Application No. 2004-042694

[Patent Document 7] Japanese Patent Application No. 2003-106231

[Patent Document 8] Japanese Patent Application No. 2003-76772

[Non-Patent Document 1] "Science" 1995, Vol. 267, page 1332

[Non-Patent Document 2] "Applied Physics Letters", 1999, Vol. 75, page 888

It is an object of the invention to provide a three-band white organic EL device having high brightness, high efficiency and high lifetime and having excellent coloring rendering properties.

The invention provides the following white organic EL device.

1. A white organic electroluminescent device comprising an emitting layer interposed between an anode and a cathode, the emitting layer emitting blue light, green light and red light, the emitting layer containing a green dopant that is an aromatic amine compound represented by formula (1),

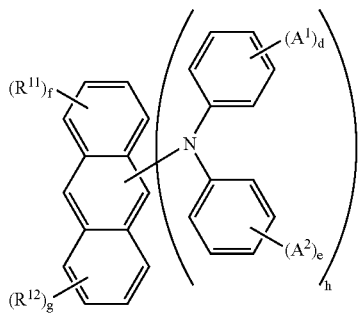 (1)

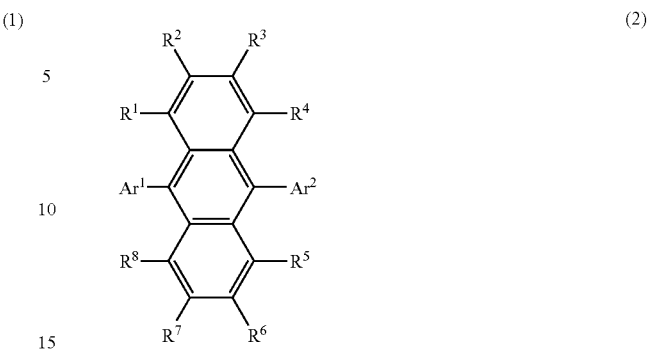 (2)

wherein $A^1$ to $A^2$ are independently a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted aryamino group having 5 to 50 nucleus carbon atoms, a substituted or unsubstituted alkylamino group having 1 to 10 carbon atoms or a halogen atom; d and e are independently an integer of 1 to 5; h is an integer of 1 to 9; when d and e are independently 2 or more, $A^1$s and $A^2$s may be the same or different and may be joined together to form a saturated or unsaturated ring; provided that compounds where both of $A^1$ and $A^2$ are hydrogen atoms are excluded;

$R^{11}$ is a substituted or unsubstituted secondary or tertiary alkyl group having 3 to 10 carbon atoms or a substituted or unsubstituted secondary or tertiary cycloalkyl group having 3 to 10 carbon atoms; f is an integer of 1 to 9; when f is 2 or more, $R^{11}$s may be the same or different; $R^{12}$ is a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted arylamino group having 5 to 50 nucleus carbon atoms, a substituted or unsubstituted alkylamino group having 1 to 10 carbon atoms, or a halogen atom; g is an integer of 0 to 8; when g is 2 or more, $R^{12}$s may be the same or different; and f+g+h is an integer of 2 to 10.

2. The white organic electroluminescent device according to 1, wherein the emitting layer has a three-layer structure of a blue emitting layer emitting blue light, a green emitting layer emitting green light and a red emitting layer emitting red light.

3. The white organic electroluminescent device according to 1, wherein the emitting layer has a two-layer structure of a blue emitting layer emitting blue light, and a green/red emitting layer emitting green light and red light.

4. The white organic electroluminescent device according to any one of 1 to 3, wherein the emitting layer contains a host material that is an unsymmetric anthracene compound.

5. The white organic electroluminescent device according to 4, wherein the unsymmetric anthracene compound is a compound represented by formula (2).

wherein $Ar^1$ and $Ar^2$ are independently a substituted or unsubstituted aryl group having 6 to 50 nucleus carbon atoms, provided that $Ar^1$ and $Ar^2$ do not have the same structure, $R^1$ to $R^8$ are independently a hydrogen atom, a substituted or unsubstituted aryl group having 6 to 50 nucleus carbon atoms, a substituted or unsubstituted aromatic heterocyclic group having 5 to 50 nucleus carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group.

6. A white organic electroluminescent device comprising an anode, an emitting layer and a cathode,
the ionization potential of a green dopant forming the emitting layer being equal to or larger than the ionization potential of a blue dopant forming the emitting layer.

7. A white organic electroluminescent device comprising in sequence an anode, a blue emitting layer, a green emitting layer, a red emitting layer and a cathode,
the ionization potential of a green dopant forming the green emitting layer being equal to or larger than the ionization potential of a blue dopant forming the blue emitting layer.

8. A white organic electroluminescent device comprising in sequence an anode, a blue emitting layer, a red emitting layer, a green emitting layer and a cathode,
the ionization potential of a green dopant forming the green emitting layer being equal to or larger than the ionization potential of a blue dopant forming the blue emitting layer.

9. The white organic electroluminescent device according to any one of 2 to 5, 7 and 8, wherein a blue dopant forming the blue emitting layer is at least one compound selected from styryl amines, amine-substituted styryl compounds, amine-substituted condensed aromatic rings and condensed-aromatic-ring containing compounds.

10. The white organic electroluminescent device according to any one of 2 to 5, 7, 8 and 9, wherein a red dopant forming the red emitting layer is a compound containing a fluoranthene skeleton or perylene skeleton.

According to the invention, there can be provided a three-band white organic EL device having high brightness, high efficiency and high lifetime and having excellent color rendering properties.

BEST MODES FOR WORKING THE INVENTION

Embodiment 1

Figure 1:
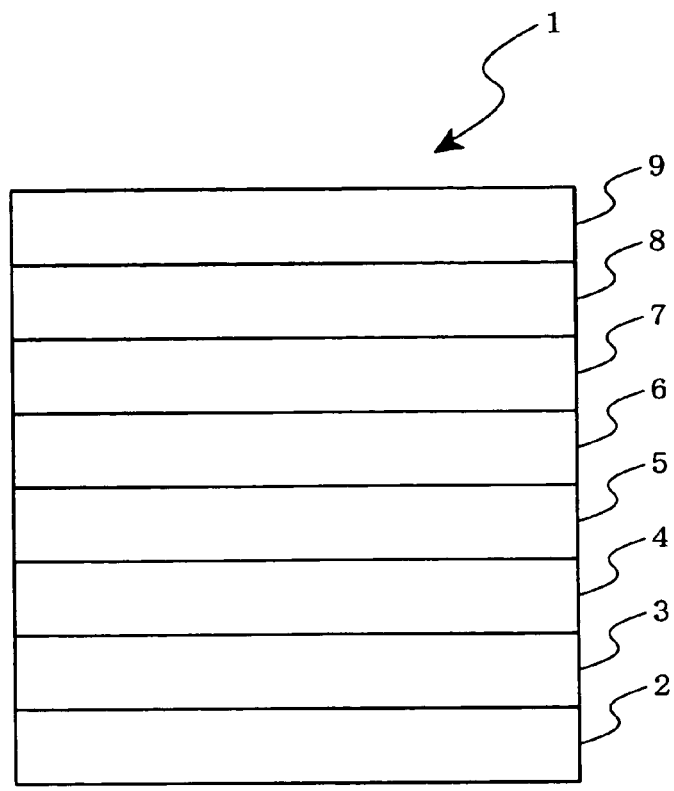
FIG. 1 is a diagram showing the constitution of a white organic EL device of Embodiment 1.
Figure 2:
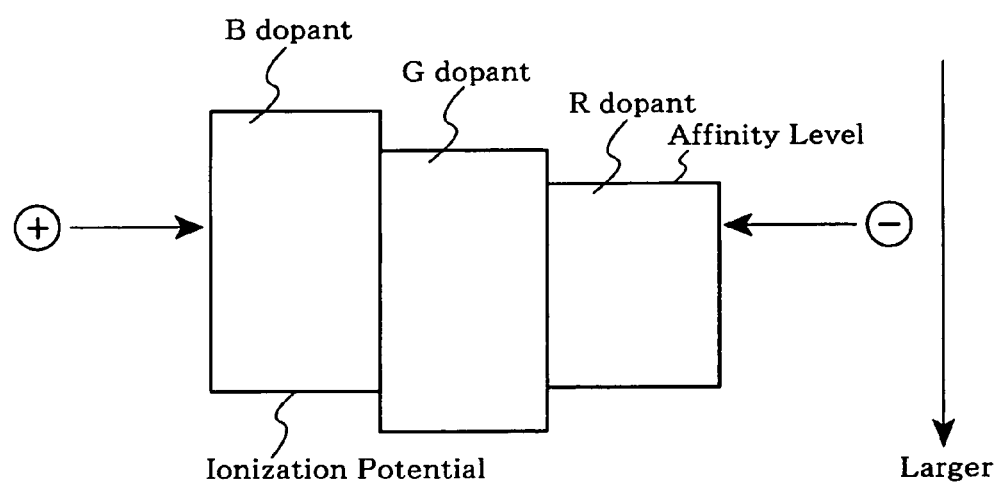
FIG. 2 is an energy level diagram of a blue dopant, a green dopant and a red dopant which form a blue emitting layer, a green emitting layer and a red emitting layer of the white organic EL device of Embodiment 1.

FIG. 1 is a diagram showing the constitution of a white organic EL device according to one embodiment of the invention. FIG. 2 is an energy level diagram of a blue (B) dopant, a green (G) dopant and a red (R) dopant which form a blue emitting layer, a green emitting layer and a red emitting layer, respectively, in the above white organic EL device.

As shown in FIG. 1, the white organic EL device 1 has a structure in which an anode 2, a hole injecting layer 3, a hole transporting layer 4, a blue emitting layer 5, a green emitting layer 6, a red emitting layer 7, an electron transporting layer 8 and a cathode 9 are stacked.

The blue emitting layer 5 contains a host material and a blue dopant, the green emitting layer 6 contains a host material and a green dopant that is an aromatic amine compound of the following formula (1), and the red emitting layer 7 contains a host material and a red dopant.

FIG. 2 shows energy levels of the blue (B) dopant, the green (G) dopant and the red (R) dopant which form the blue emitting layer 5, the green emitting layer 6 and the red emitting layer 7 of the white organic EL device 1, respectively. In this Figure, upper sides represent levels (affinity levels: Af) of LUMO of the dopants of the emitting layers, and lower sides similarly represent levels (ionization potentials: Ip) of HOMO thereof. In this energy level diagram, a lower portion exhibits a greater value as shown by an arrow with respect to the energy level of holes. In FIG. 2, − represent electrons, and + represents holes.

As shown in FIG. 2, preferably, the ionization potential of the green dopant that forms the green emitting layer 6 is equal to, or greater than, that of the blue dopant that forms the blue emitting layer 5. The term "equal" as used herein means that the injection of holes from the blue emitting layer, etc., which is characteristic of the green dopant that is an aromatic amine compound of the following formula (1), is excellent or that the accumulation of electrons is adequately performed between the blue and green emitting layers. Specifically, the ionization potential of the green dopant may be smaller than that of the blue dopant by 0.1 to 0.2 eV.

When the dopant concentration in an emitting layer is increased, there are some cases where it is required to take account of transfer of carriers, holes or electrons, of the dopant while such is dependent upon the ionization potential or affinity level thereof. As far as the currently used carrier concentration of a dopant is concerned, it appears that it is required to take the above into account.

In FIGS. 1 and 2, electrons are injected or transported from the cathode 9 along LUMO of each dopant, that is, the affinity level in FIG. 2. In the green dopant that is an aromatic amine compound according to the invention, the ionization potential thereof is large, so that the affinity level is large as compared with other green dopants. That is, the LUMO level is lowered, and the barrier against electron injection between the green and red emitting layers (from the red emitting layer to the green emitting layer) can then be relatively small. On the other hand, since the affinity level of the blue dopant generally has a small value, there is a large barrier against injection between the blue and green emitting layers (from the green emitting layer to the blue emitting layer), which results in effective accumulation of electrons in the green emitting layer or the blue and green emitting layers.

A preferred electron level of the green dopant in FIG. 2 will be explained below.

When the ionization potential of the green dopant is $Ip_g$, and the ionization potential of the blue dopant is $Ip_b$, preferably, $Ip_g$ satisfies $Ip_g \geq Ip_b - 0.2$ by taking account of the injection of holes from the blue dopant and the host material. Specifically, $Ip_g$ is preferably 5.4 eV or higher, more preferably 5.4 to 5.8 eV.

Further, when the affinity level of the green dopant is $Af_g$, the affinity level of the blue dopant is $Af_b$ and the affinity level of the red dopant is $Af_r$, preferably, $Af_g$ is larger than $Af_b$ and smaller than $Af_r$. That is, it is preferred to satisfy $Af_b < Af_g < Af_r$. Specifically, $Af_g$ is preferably 2.8 to 3.4 eV.

Further, the energy gap ($Eg_g$) of the green dopant is preferably 2.4 to 2.6 eV.

In FIGS. 1 and 2, holes transported from the anode 2 through the hole injecting layer 3 and the hole transporting layer 4 are injected directly into the host material or the blue dopant owing to the power of an electric field. In this case, since the green dopant is an aromatic amine compound having hole transporting properties, the ionization potential thereof is large, and it is as large as that of the blue dopant. Therefore, there is almost no barrier against the injection of holes from the blue emitting layer to the green emitting layer, so that holes are excellently injected. In the next injection of holes from the green emitting layer to the red emitting layer, generally, no barrier exists, and the injection is excellent.

When such a green dopant is used, therefore, there is the feature concerning the hole injection-transportation that no particularly large hole injection barrier is formed, so that an increase in driving voltage can be obviated.

In view of the above features of injection and transportation of holes and electrons, such a green dopant enables the recombination center (excited state) of electrons and holes to be properly set and localized in the green emitting layer containing the green dopant without causing a great increase in driving voltage, and there can be obtained stable green emission with a high efficiency that is the greatest in visibility among red, green and blue. As a consequence, there can be obtained a three-band white organic EL device having high efficiency and high lifetime.

In the white organic EL device 1 of this embodiment, the blue emitting layer 5, the green emitting layer 6 and the red emitting layer 7 are stacked from the anode side in this order. However, the blue emitting layer 5, the red emitting layer 7 and the green emitting layer 6 may be stacked from the anode side in this order.

In this case, with regard to the conduction of holes, the hole barrier present between the red emitting layer and the green emitting layer comes to be relatively small. On the other hand, with regard to the conduction of electrons, a barrier exists against the injection of electrons between the blue emitting layer and the red emitting layer.

Embodiment 2

Figure 3:
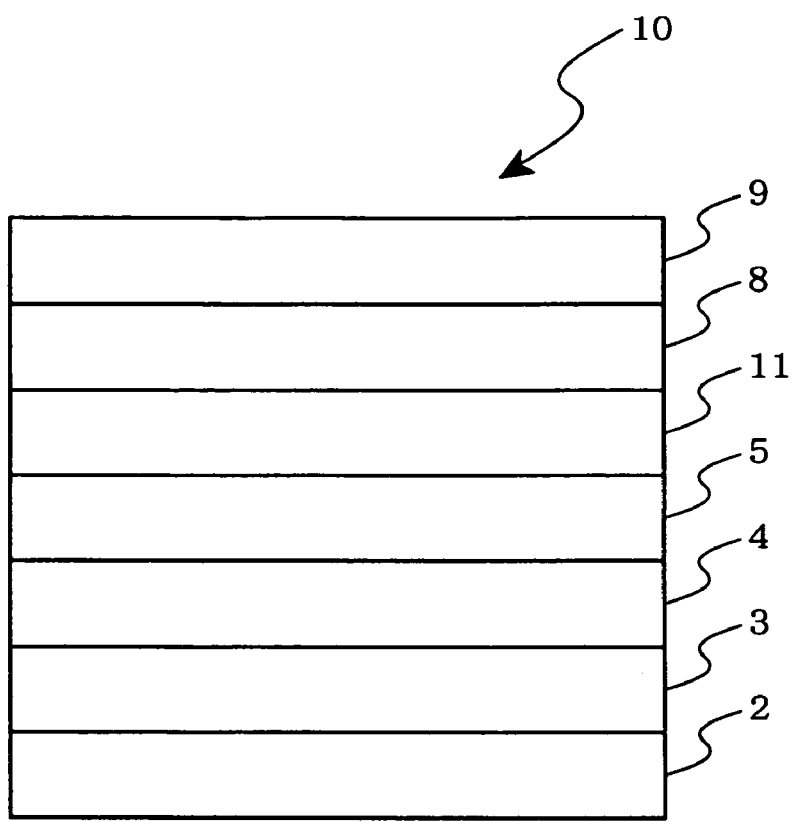
FIG. 3 is a diagram showing the constitution of a white organic EL device of Embodiment 2.

FIG. 3 is a diagram showing the constitution of a white organic EL device according to another embodiment of the invention. As shown in this Figure, a white organic EL device 10 has a structure in which an anode 2, a hole injecting layer 3, a hole transporting layer 4, a blue emitting layer 5, a green/red emitting layer 11, an electron transporting layer 8 and a cathode 9 are stacked. That is, the white organic EL device 10 of this embodiment differs from the white organic EL device 1 of embodiment 1 in that the green/red emitting layer 11 is provided in place of the green emitting layer 6 and the red emitting layer 7.

The blue emitting layer 5 contains a host material and a blue dopant, and the green/red emitting layer 11 contains a host material, a green dopant that is an aromatic amine compound of the following formula (1) and a red dopant.

In the white organic EL device 10 of this embodiment, the blue emitting layer 5 and the green/red emitting layer 11 are stacked from the anode side in this order. However, the green/red emitting layer 11 and the blue emitting layer 5 may be stacked from the anode side in this order.

In the white organic EL device of the invention, an emitting layer is interposed between the anode and the cathode as described above, and the emitting layer emits blue light, green light and red light. Further, the emitting layer contains the green dopant that is the aromatic amine compound of the following formula (1). The ionization potential of the green dopant is preferably equal to, or greater than, the ionization potential of the blue dopant as described above. The emitting layer may be formed of a single layer or a plurality of layers. Further, another organic layer or inorganic layer may be interposed between the anode and an emitting layer, between an emitting layer and the cathode or between emitting layers. Such an interposed layer is not particularly limited so long as it can transport electrons and holes and has light transmissivity. In the organic EL device of the invention, light can be extracted through the anode or the cathode.

Examples of preferred white organic EL device structures of the invention are as follows.

(1) An anode, a hole-injecting layer, a hole-transporting layer, a blue/green/red emitting layer, an electron-transporting layer, an electron-injecting layer, and a cathode (2) An anode, a hole-injecting layer, a hole-transporting layer, a blue emitting layer, a green/red emitting layer, an electron-transporting layer, an electron-injecting layer and a cathode (3) An anode, a hole-injecting layer, a hole-transporting layer, a green/red emitting layer, a blue emitting layer, an electron-transporting layer, an electron-injecting layer and a cathode (4) An anode, a hole-injecting layer, a hole-transporting layer, a blue emitting layer, a green emitting layer, a red emitting layer, an electron-transporting layer, an electron-injecting layer and a cathode (5) An anode, a hole-injecting layer, a hole-transporting layer, a blue emitting layer, a red emitting layer, a green emitting layer, an electron-transporting layer, an electron-injecting layer and a cathode (1) is a device where an emitting layer is a single layer of blue/green/red emitting layer; (2) and (3) are devices where an emitting layer has a two-layer structure of a blue emitting layer and a green/red emitting layer; (4) and (5) are devices where an emitting layer has a three-layer structure of a blue emitting layer, a green emitting layer, and a red emitting layer.

A green emitting layer, a blue emitting layer, a red emitting layer and a green/red emitting layer, which are characteristic parts of the invention, are described below.

A green emitting layer is preferably an emitting layer which emits light with a maximum wavelength of 500 to 570 nm and contains a host material and green dopant of an aromatic amine compound represented by formula (1).

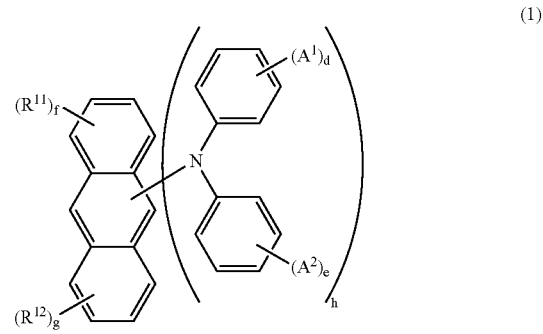

wherein $A^1$ to $A^2$ are independently a hydrogen atom, a substituted or unsubstituted alkyl group having 1 to 10 carbon atoms (preferably 1 to 6 carbon atoms), a substituted or unsubstituted aryl group having 5 to 50 nucleus carbon atoms (preferably 5 to 10 nucleus carbon atoms, a substituted or unsubstituted cycloalkyl group having 3 to 20 nucleus carbon atoms (preferably 5 to 10 carbon atoms), a substituted or unsubstituted alkoxy group having 1 to 10 carbon atoms (preferably 1 to 6 carbon atoms), a substituted or unsubstituted aryloxy group having 5 to 50 nucleus carbon atoms (preferably 5 to 10 nucleus carbon atoms), a substituted or unsubstituted arylamino group having 5 to 50 nucleus carbon atoms (preferably 5 to 20 nucleus carbon atoms), a substituted or unsubstituted alkylamino group having 1 to 10 carbon atoms (preferably 1 to 6 carbon atoms), or a halogen atom.

A substituted or unsubstituted alkyl group of $A^1$ to $A^2$ includes methyl, ethyl, propyl, isopropyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphenylmethyl, and α-benzyloxybenzyl groups.

A substituted or unsubstituted aryl group of $A^1$ to $A^2$ includes phenyl, 2-methylphenyl, 3-methylphenyl, 4-methylphenyl, 4-ethylphenyl, biphenyl, 4-methylbiphenyl, 4-ethylbiphenyl, 4-cyclohexylbiphenyl, terphenyl, 3,5-dichlorophenyl, naphtyl, 5-methylnaphtyl, anthryl, and pyrenyl groups.

A substituted or unsubstituted cycloalkyl group of $A^1$ to $A^2$ includes cyclopropyl, cyclobutyl, cyclopentyl, cyclohexyl, norbornyl, and adamantyl groups.

A substituted or unsubstituted alkoxy group of $A^1$ to $A^2$ includes methoxy, ethoxy, propoxy, isopropoxy, butoxy, isobutoxy, sec-butoxy, tert-butoxy, various pentyloxy, and various hexyloxy groups.

A substituted or unsubstituted aryloxy group of $A^1$ to $A^2$ includes phenoxy, tolyloxy, and naphthyloxy groups.

A substituted or unsubstituted arylamino group of $A^1$ to $A^2$ includes diphenylamino, ditolylamino, dinaphthylamino, and naphthylphenylamino groups.

A substituted or unsubstituted alkylamino group of $A^1$ to $A^2$ includes dimethylamino, diethylamino, and dihexylamino groups.

A halogen atom of $A^1$ to $A^2$ includes fluoride, chlorine, and bromine atoms.

In formula (1), $A^1$ and $A^2$ cannot be hydrogen atoms at the same time.

In formula (1), d and e are each an integer of 1 to 5, preferably 1 to 3. When d and e are each 2 or more, $A^1$s and $A^2$s may be the same or different. They may be joined together to form a saturated or unsaturated ring. h is an integer of 1 to 9, preferably 1 to 3.

$R^{11}$ is a substituted or unsubstituted secondary or tertiary alkyl group having 3 to 10 carbon atoms or a substituted or unsubstituted secondary or tertiary cycloalkyl group having 3 to 10 carbon atoms.

The substituted or unsubstituted secondary or tertiary alkyl group having 3 to 10 carbon atoms of $R^{11}$ includes isopropyl, tert-butyl, sec-butyl, tert-pentyl, 1-methylbutyl, 1-methylpentyl, 1,1'-dimethylpentyl, 1,1'-diethylpropyl, 1-benzyl-2-phenylethyl, 1-methoxyethyl, and 1-phenyl-1-methylethyl groups.

The substituted or unsubstituted secondary or tertiary cycloalkyl group having 3 to 10 carbon atoms of $R^{11}$ includes cyclopentyl, cyclohexyl, norbornyl, and adamantyl groups.

In formula (1), f is an integer of 1 to 9, preferably 1 to 3. When f is 2 or more, $R^{11}$s may be the same or different.

$R^{12}$ is a hydrogen atom, a substituted or unsubstituted alkyl group having 1 to 10 carbon atoms (preferably 1 to 6 carbon atoms), a substituted or unsubstituted aryl group having 5 to 50 nucleus carbon atoms (preferably 5 to 10 nucleus carbon atoms), a substituted or unsubstituted cycloalkyl group having 3 to 20 nucleus carbon atoms (preferably 5 to 10 nucleus carbon atoms), a substituted or unsubstituted alkoxy group having 1 to 10 carbon atoms (preferably 1 to 6 carbon atoms), a substituted or unsubstituted aryloxy group having 5 to 50 nucleus carbon atoms (preferably 5 to 10 nucleus carbon atoms), a substituted or unsubstituted arylamino group having 5 to 50 nucleus carbon atoms (preferably 5 to 20 nucleus carbon atoms), a substituted or unsubstituted alkylamino group having 1 to 10 carbon atoms (preferably 1 to 6 carbon atoms), or a halogen atom.

Examples of the substituted or unsubstituted alkyl, aryl, cycloalkyl, alkoxy, aryloxy, arylamino, and alkylamino groups and halogen atom of $R^{12}$ include the same groups and atoms as those of $A^1$ to $A^2$ mentioned above.

In formula (3), g is an integer of 0 to 8 and preferably 0 to 2.

When g is 2 or more, $R^{12}$s may be the same or different.

In formula (1), f+g+h is an integer of 2 to 10 and preferably 2 to 6.

More preferred are compounds represented by formulas (1-1) to (1-7) as the aromatic amine compound.

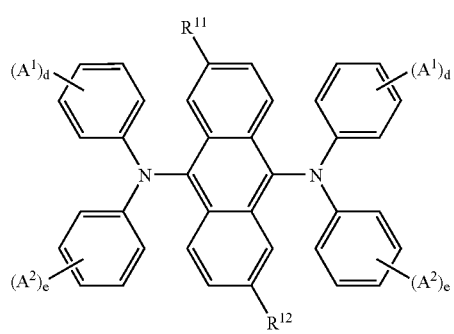

(1-1)

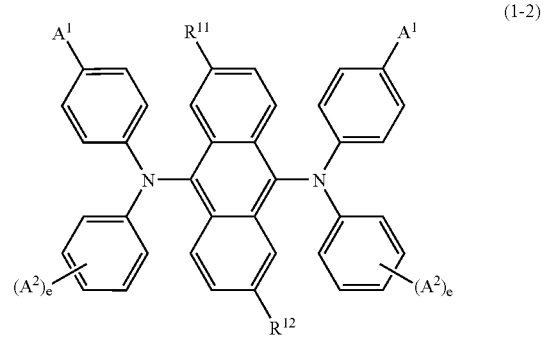

(1-2)

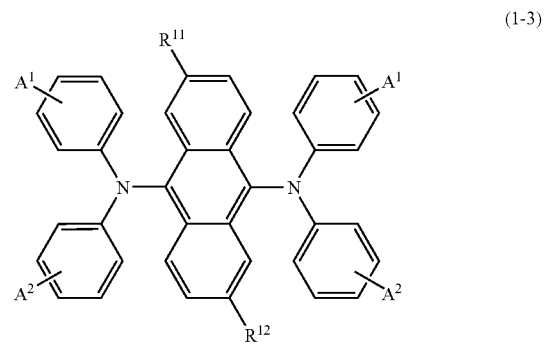

(1-3)

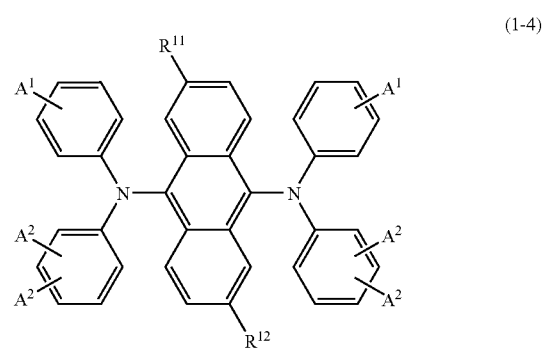

(1-4)

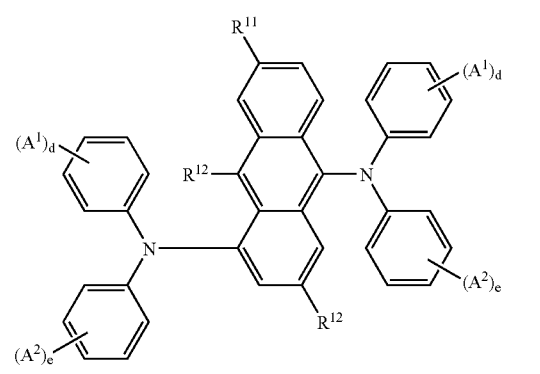

(1-5)

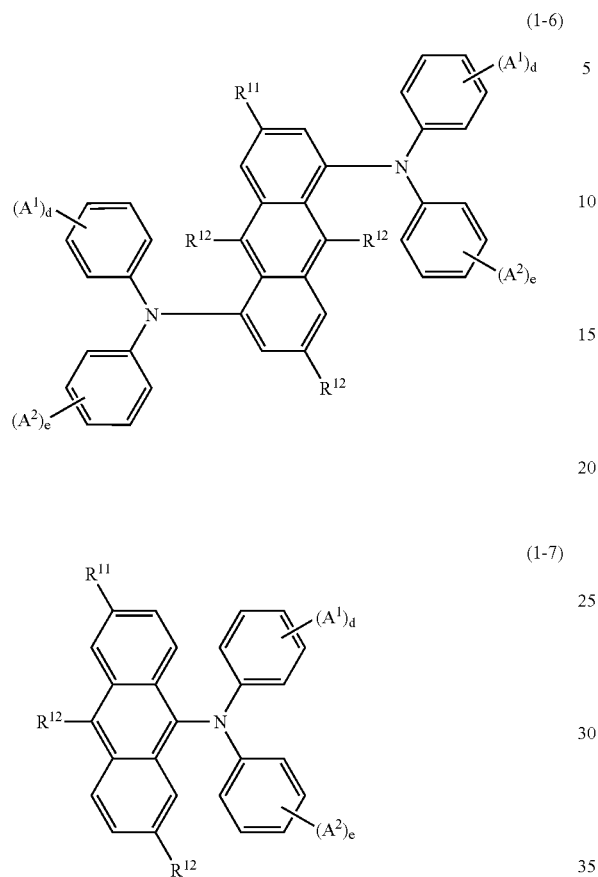
In formulas (1-1) to (1-7), $A^1$, $A^2$, p, q, $R^{11}$ and $R^{12}$ are the same as those in formula (1).
Specific examples of the aromatic amine compound are shown below. The compounds used in the invention are not limited to the exemplified compounds. Me is a methyl group.
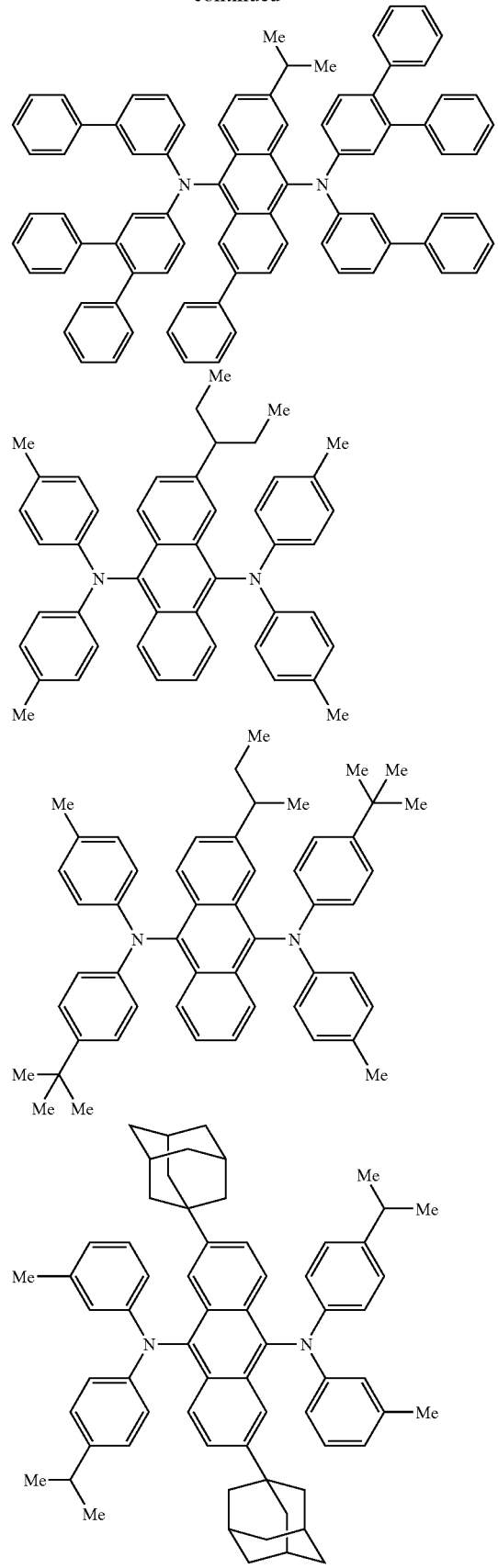
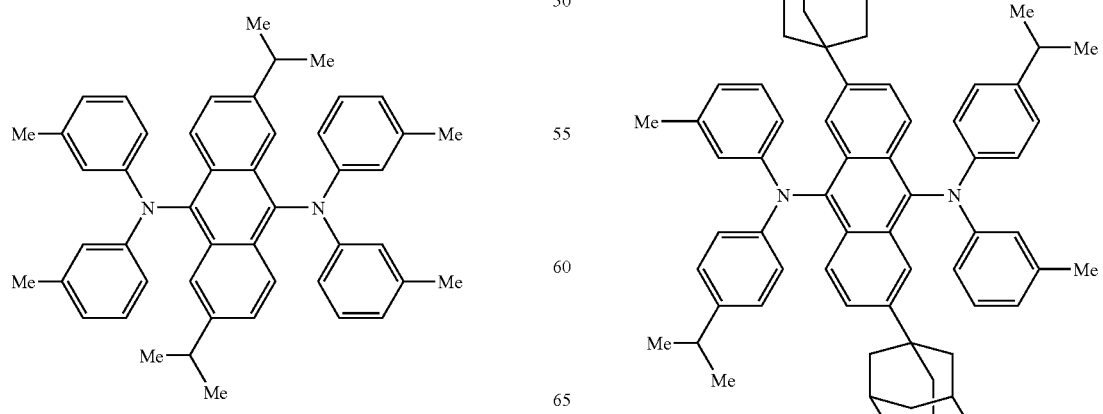

-continued
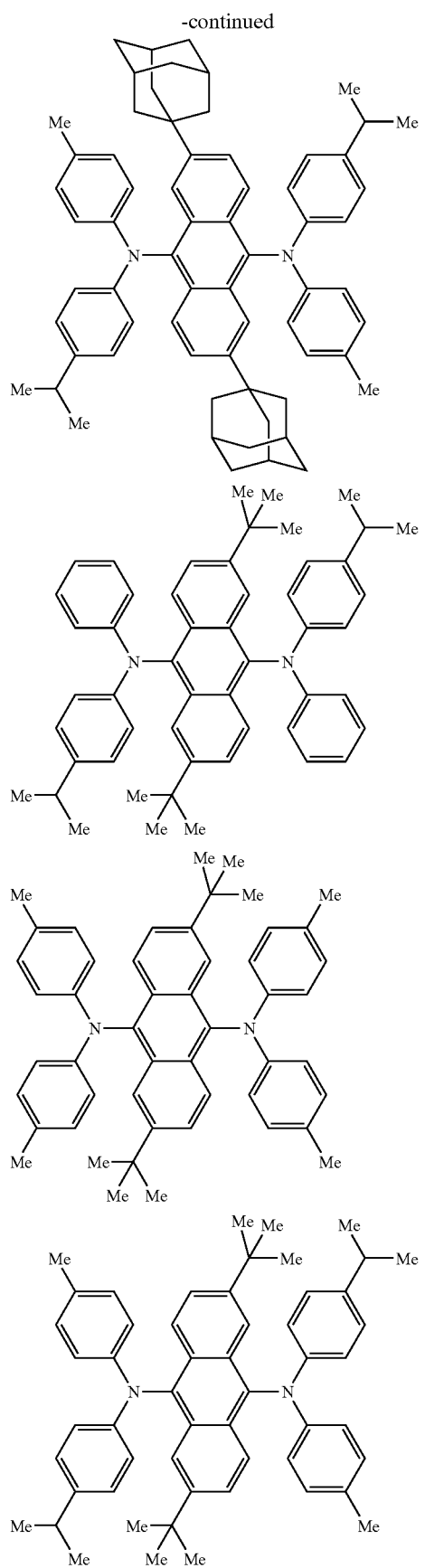
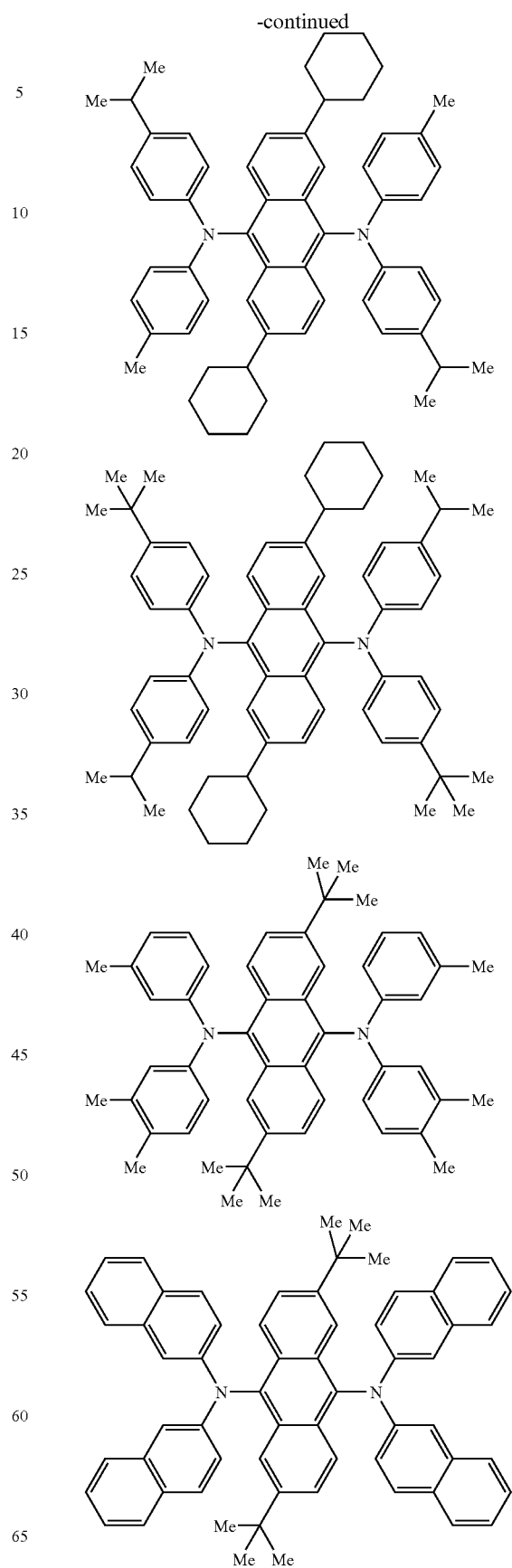

-continued
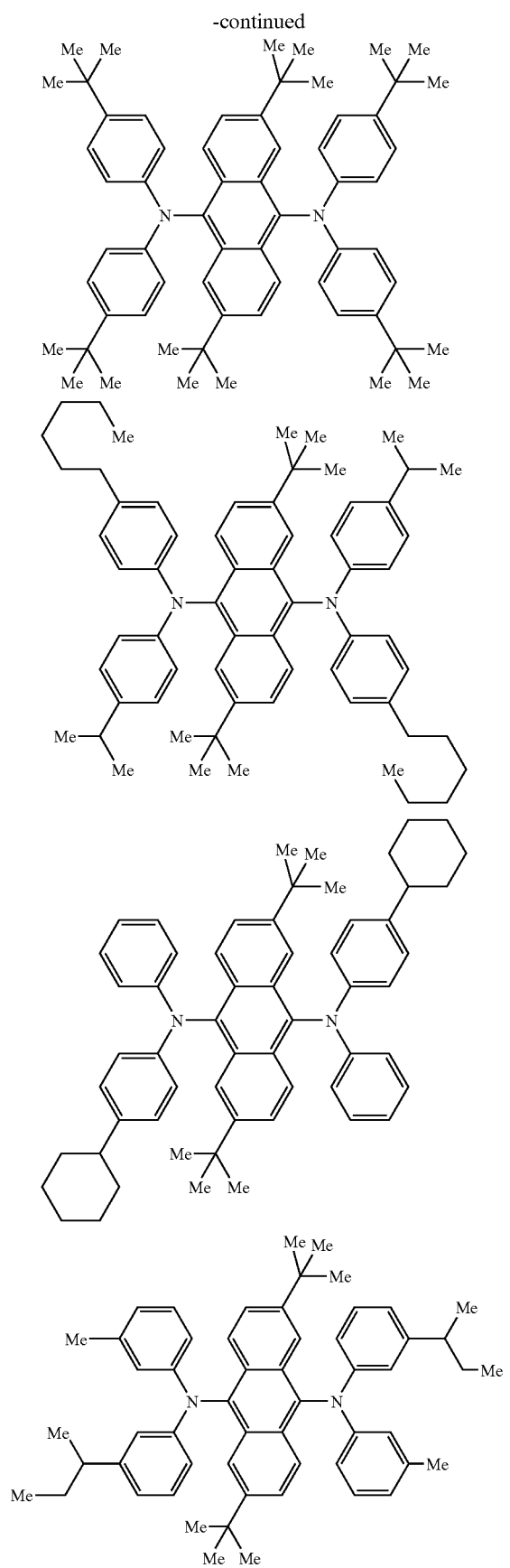
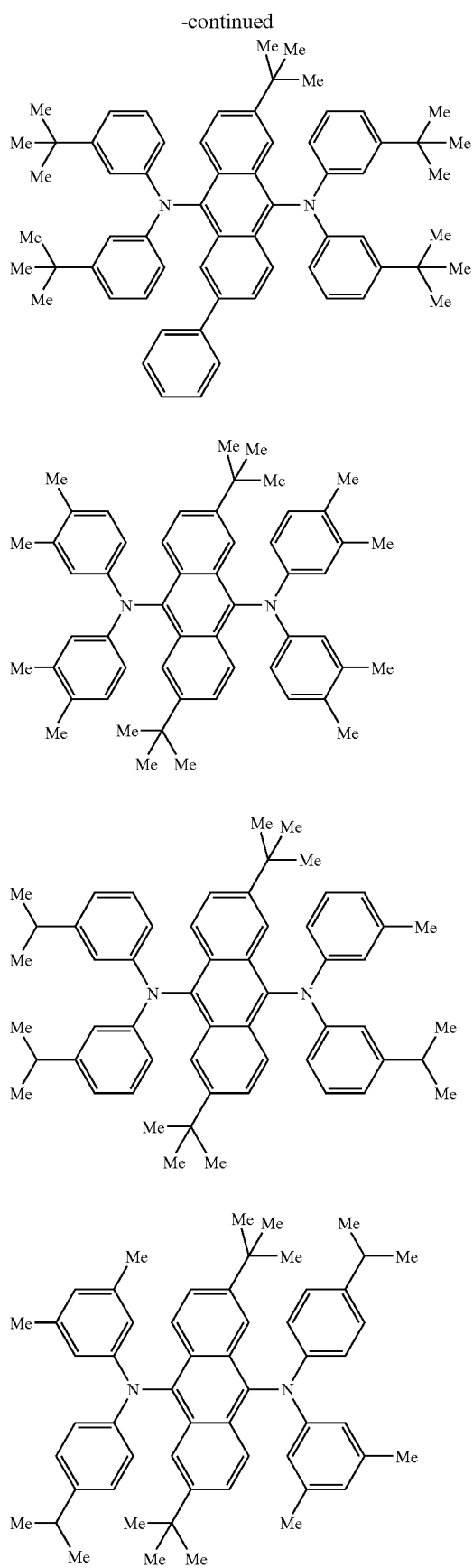

-continued
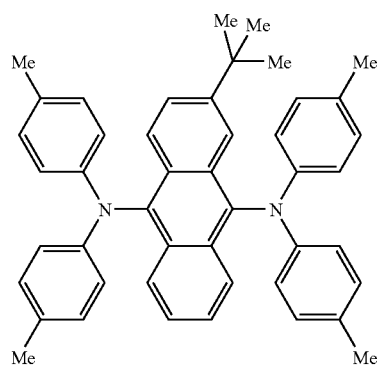
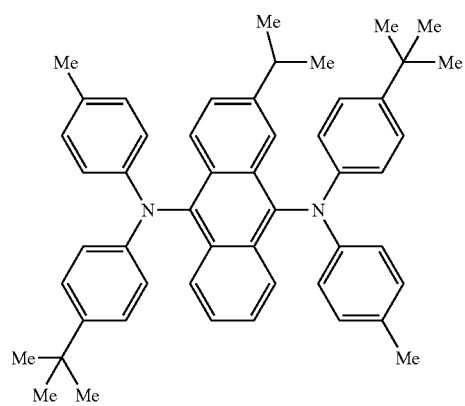
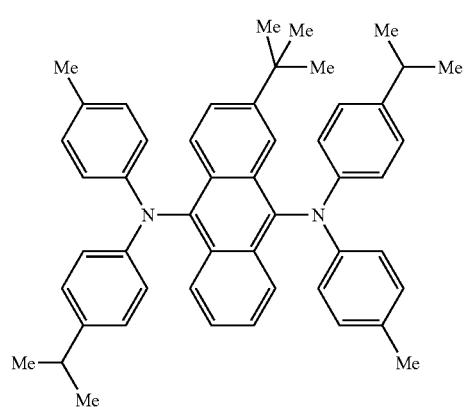
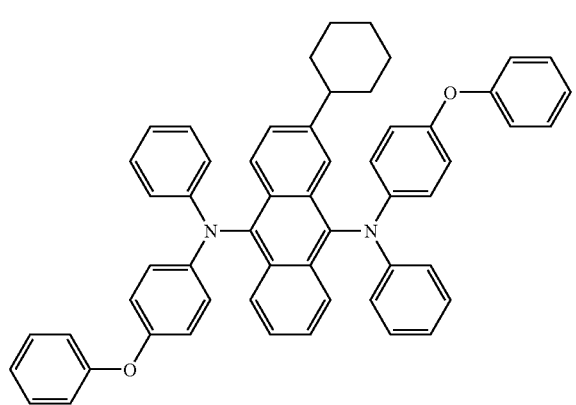
-continued
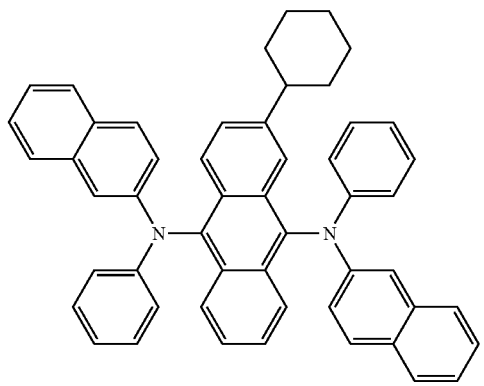
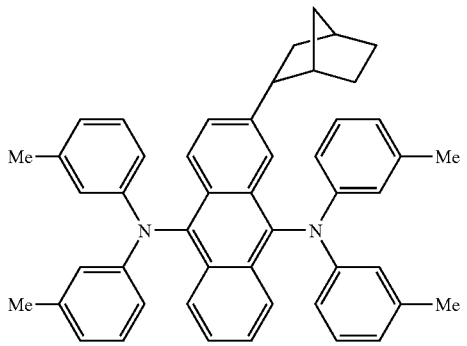
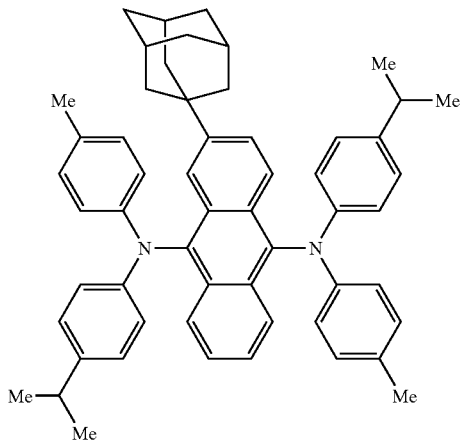
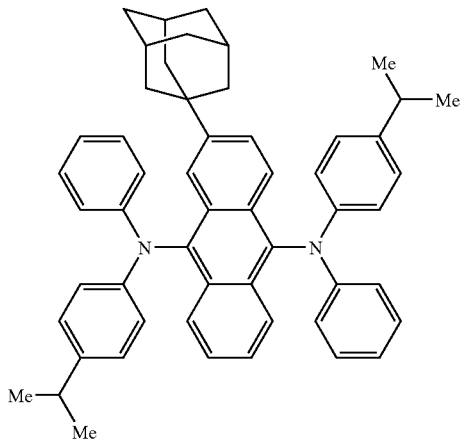

-continued
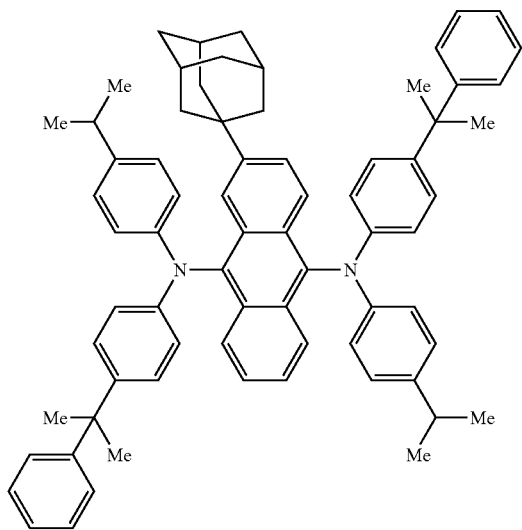
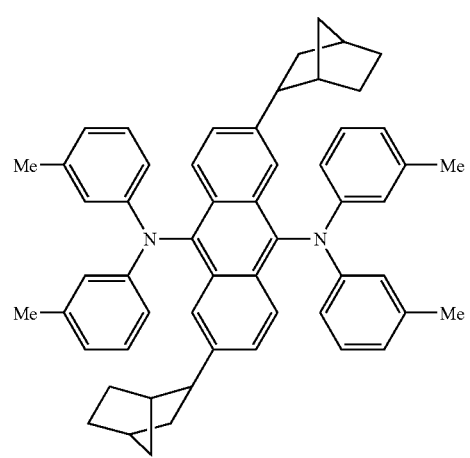
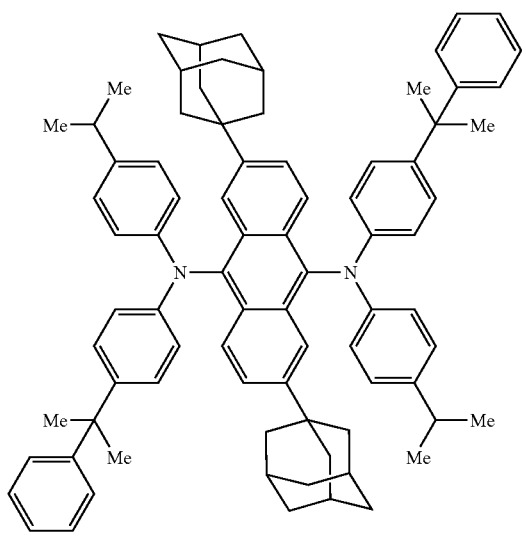
-continued
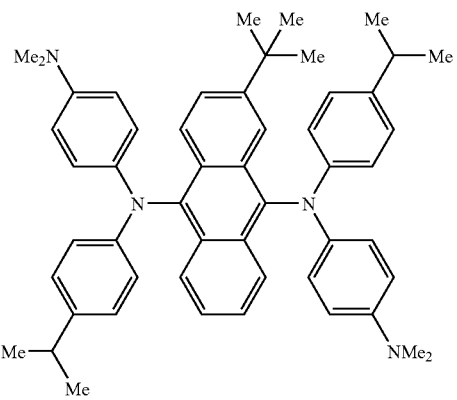
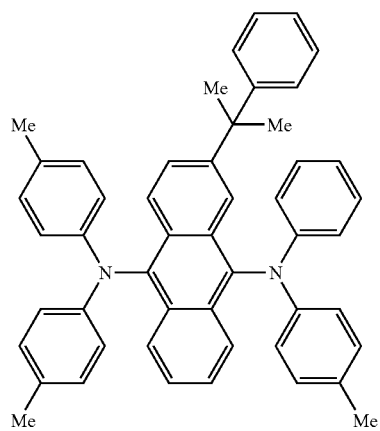
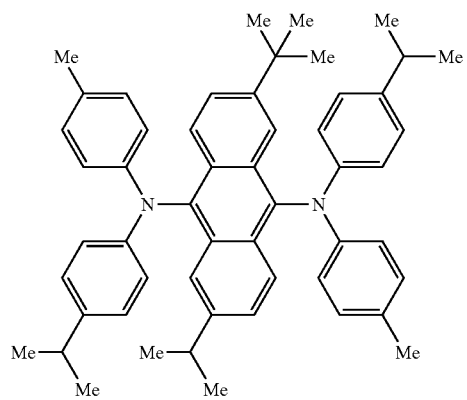
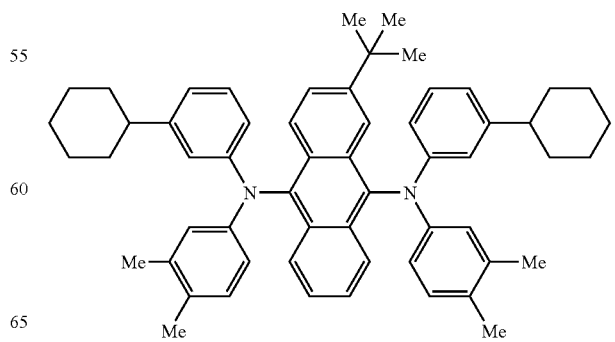

-continued
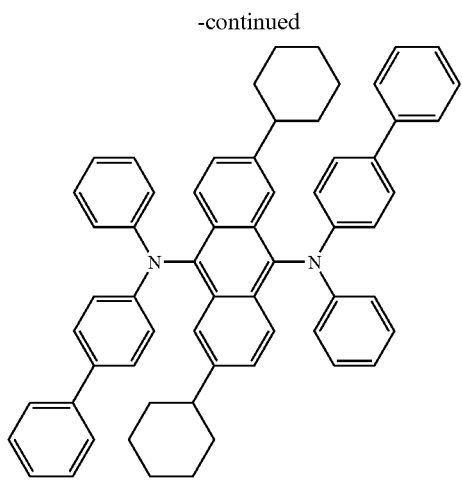
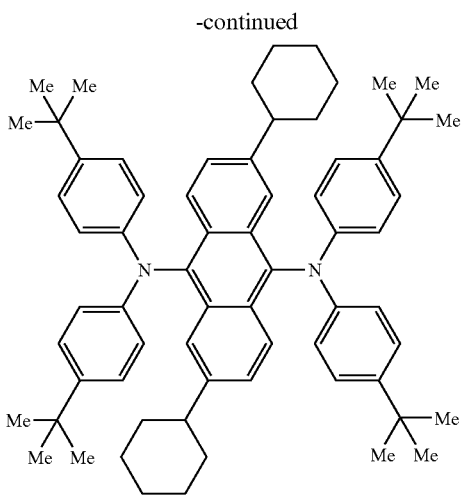
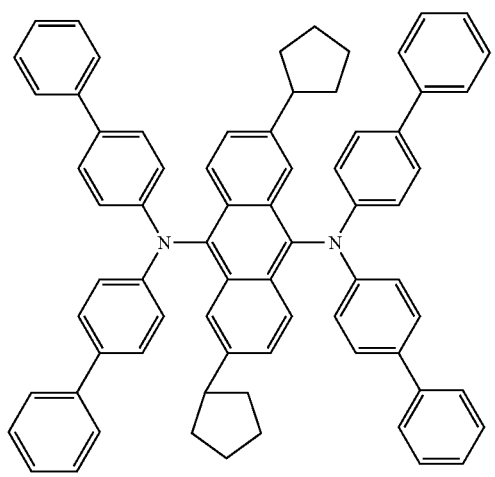
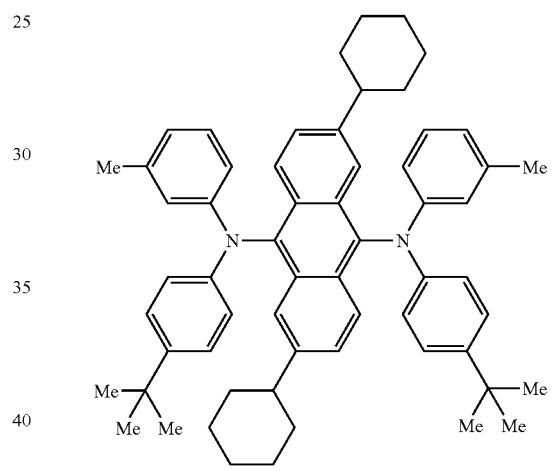
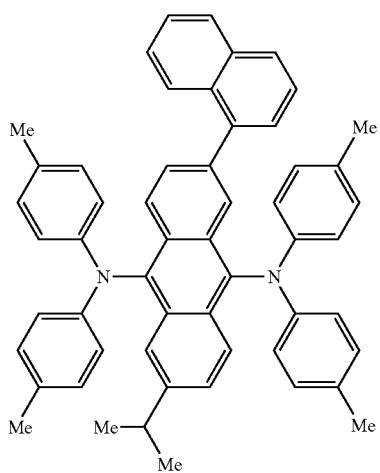
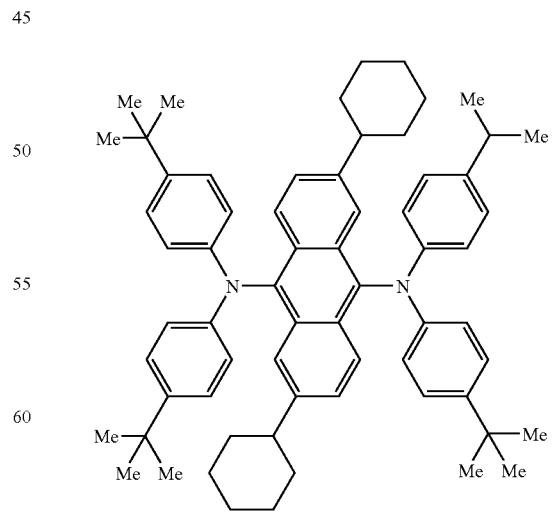

-continued
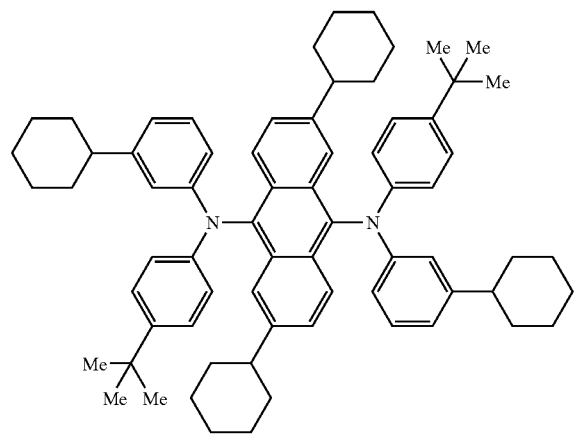
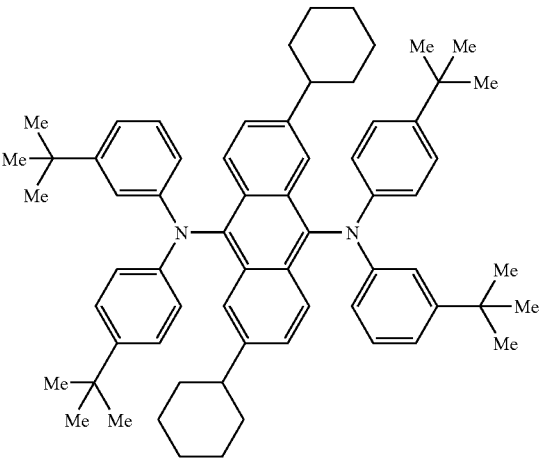
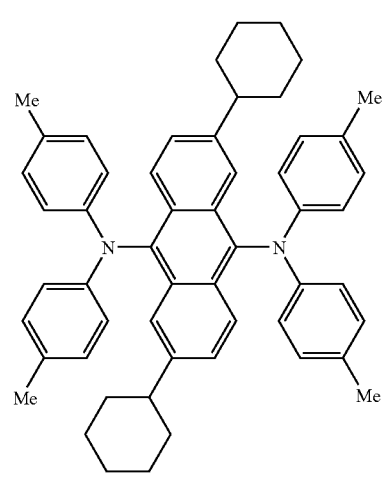
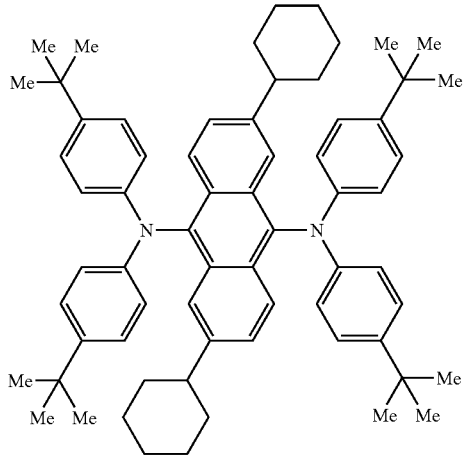
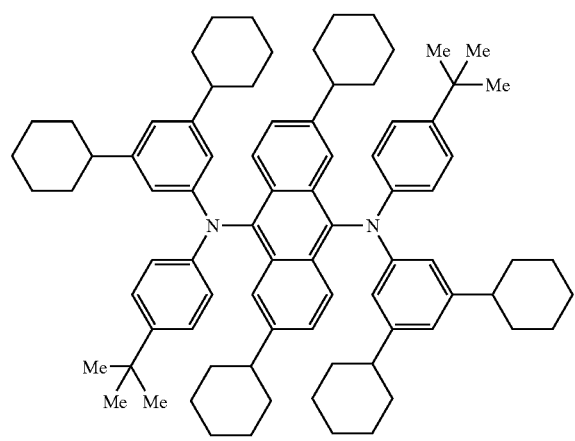
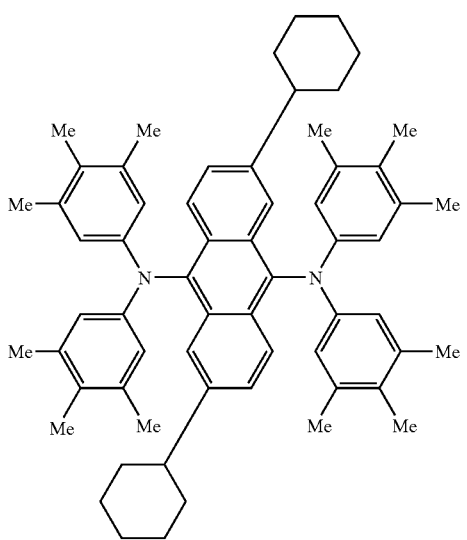

-continued
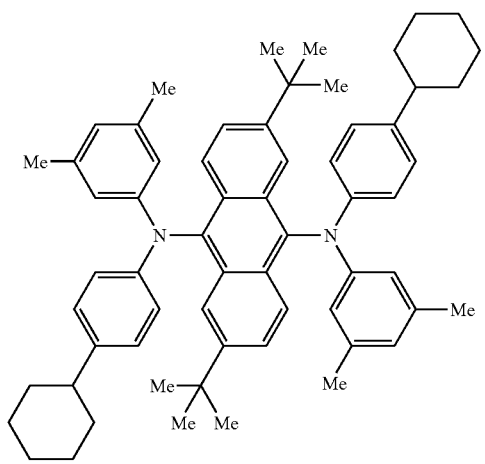
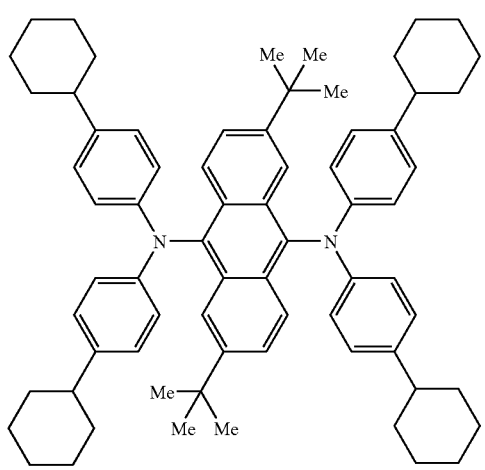
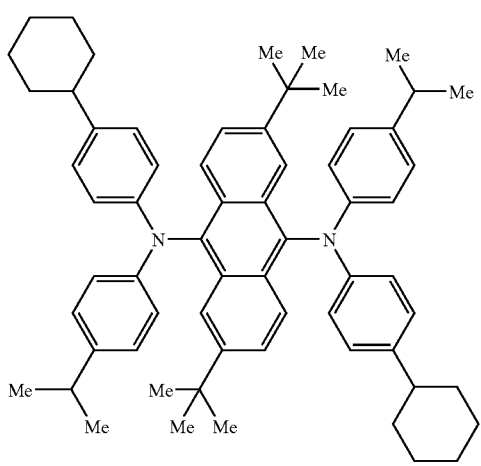
-continued
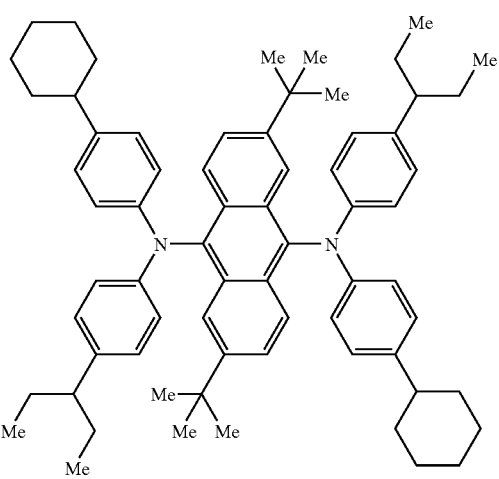
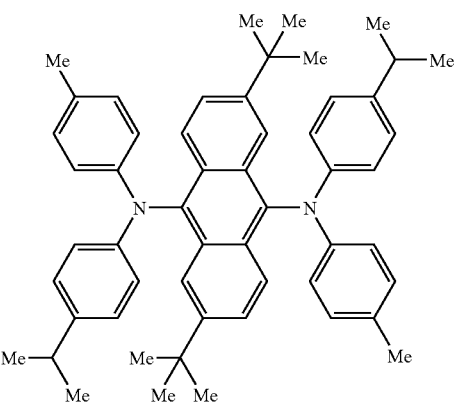
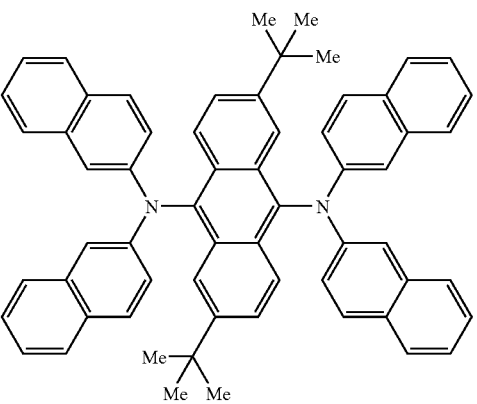

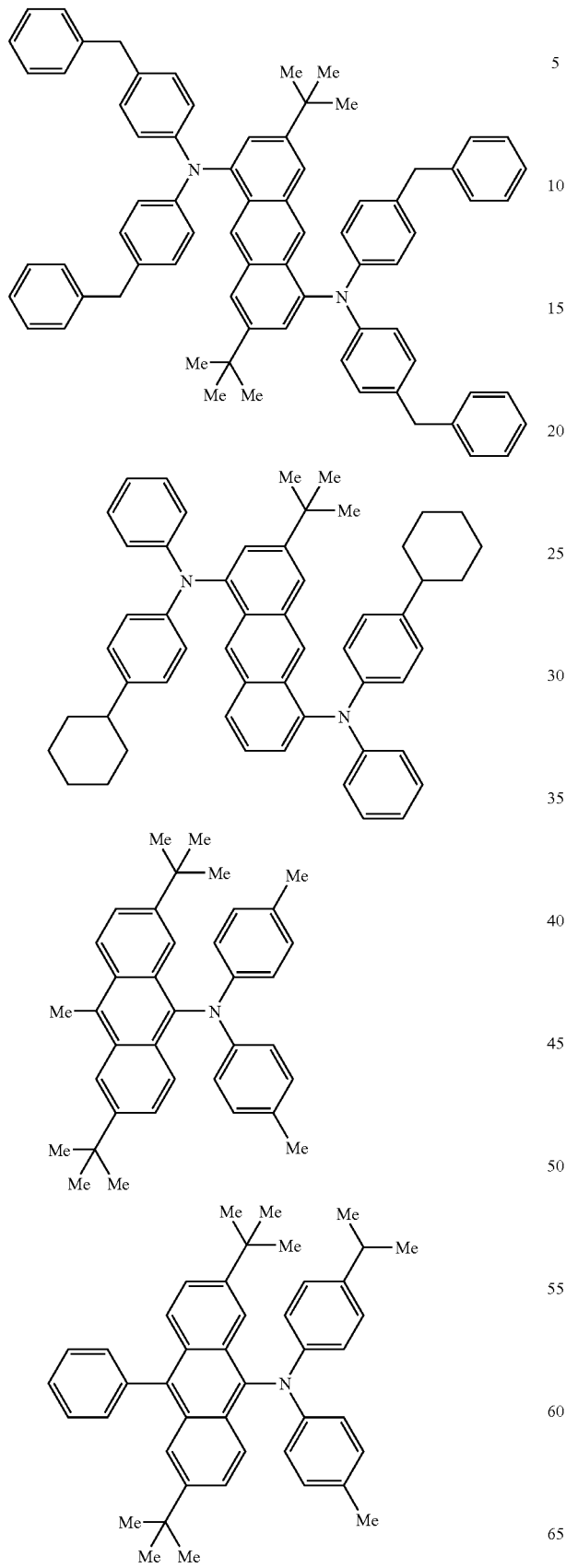
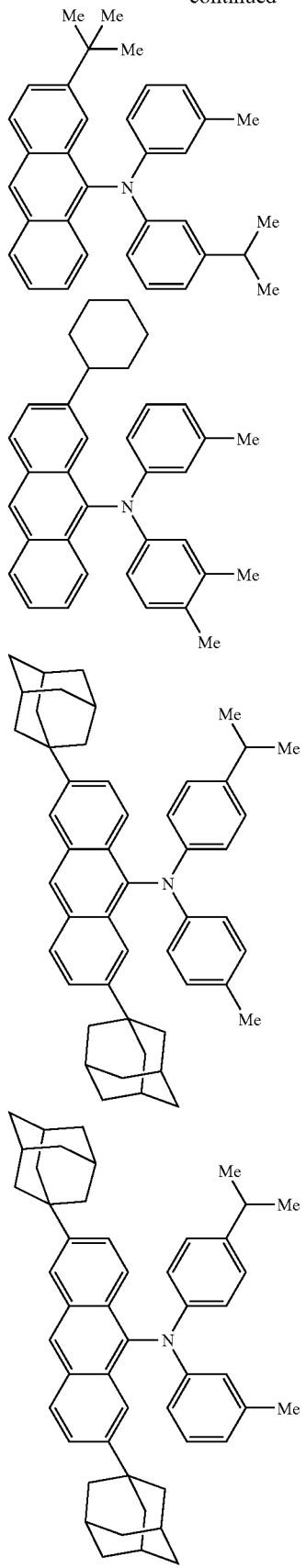

-continued

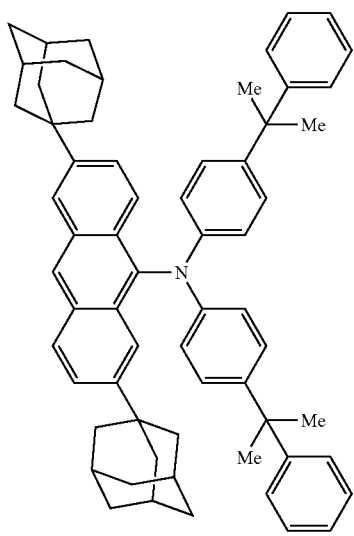

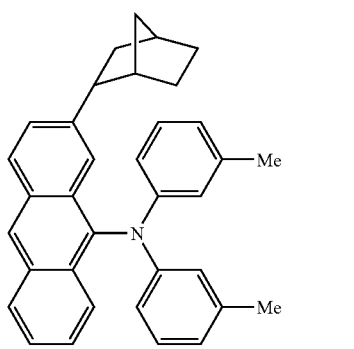

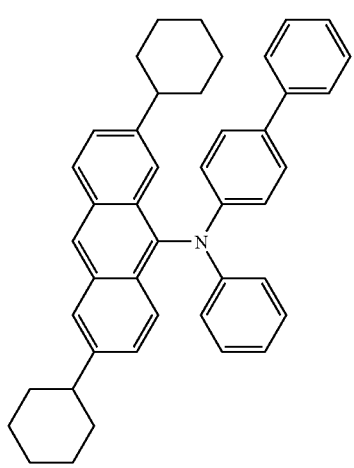

-continued

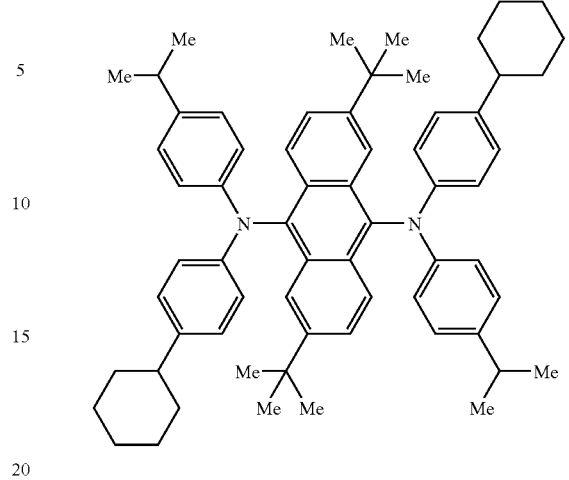

The above-mentioned green dopants can be produced as shown in Japanese Patent Application No. 2003-106231.

The content of a green dopant contained in a green emitting layer is preferably 0.25 to 25 wt % and more preferably 1.25 to 12.5 wt %.

A host material is not particularly limited and the following can be suitably used; anthracene compounds, piren compounds, chrysene compounds, unsymmetric compounds thereof.

Among these, anthracene compounds, especially unsymmetric anthracene compounds are preferable. Compounds represented by formula (2) are preferable as unsymmetric anthracene compounds

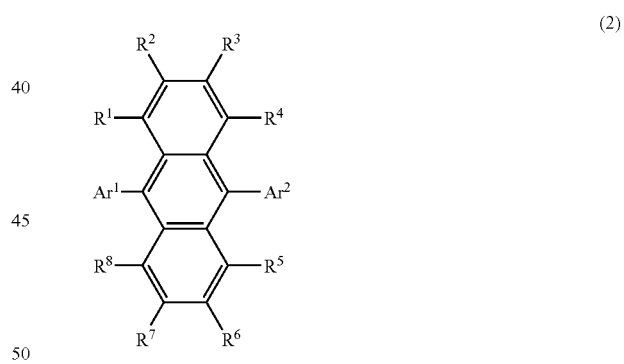

(2)

wherein $Ar^1$ and $Ar^2$ are independently a substituted or unsubstituted aryl group having 6 to 50 nucleus carbon atoms, provided that $Ar^1$ and $Ar^2$ do not have the same structure.

$R^1$ to $R^8$ are independently a hydrogen atom, a substituted or unsubstituted aryl group having 6 to 50 nucleus carbon atoms, a substituted or unsubstituted aromatic heterocyclic group having 5 to 50 nucleus carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group.

Examples of the substituted or unsubstituted aryl group of $Ar^1$ and $Ar^2$ in formula (2) include phenyl, 1-naphthyl, 2-naphtyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pirenyl, 2-pirenyl, 4-pirenyl, 2-biphenylyl, 3-biphenylyl, 4-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphtyl, 4-methyl-1-naphtyl, 4-methyl-1-anthryl, 4'-methylbiphenylyl and 4"-t-butyl-p-terphenyl-4-yl groups.

Examples of the substituted or unsubstituted aryl group of $R^1$ to $R^8$ in formula (2) include the same groups as the above-mentioned groups for $Ar^1$ and $Ar^2$.

Examples of the substituted or unsubstituted aromatic hetrocyclic group of $R^1$ to $R^8$ in formula (2) include 1-pyrrolyl, 2-pyrrolyl, 3-pyrrolyl, pyrazinyl, 2-pyrazinyl, 3-pyrazinyl, 4-pyrazinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthrezinyl, 2-phenanthrezinyl, 3-phenanthrezinyl, 4-phenanthrezinyl, 6-phenanthrezinyl, 7-phenanthrezinyl, 8-phenanthrezinyl, 9-phenanthrezinyl, 10-phenanthrezinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl1-indolyl, 4-t-butyl1-indolyl, 2-t-butyl3-indolyl and 4-t-butyl3-indolyl groups.

Examples of the substituted or unsubstituted alkyl group of $R^1$ to $R^8$ in formula (2) include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diisodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-nobornyl, and 2-nobornyl groups.

The substituted or unsubstituted alkoxy group of $R^1$ to $R^8$ in formula (2) are represented by —OY. Examples of Y include the same groups as the above-mentioned substituted or unsubstituted alkyl groups.

Examples of the substituted or unsubstituted aralkyl group of $R^1$ to $R^8$ in formula (2) include the above-mentioned alkyl groups which are substituted by the above-mentioned substituted or unsubstituted aryl groups.

The substituted or unsubstituted aryloxy group of $R^1$ to $R^8$ in formula (2) is represented by —OY'. Examples of Y' include the same groups as the above-mentioned substituted or unsubstituted aryl groups.

The substituted or unsubstituted arylthio group of $R^1$ to $R^8$ in formula (2) is represented by —OY'. Examples of Y' include the same groups as the above-mentioned substituted or unsubstituted alkyl groups.

The substituted or unsubstituted alkoxycarbonyl group of $R^1$ to $R^8$ in formula (2) is represented by —COOY. Examples of Y include the same groups as the above-mentioned substituted or unsubstituted alkyl groups.

The substituted or unsubstituted silyl group of $R^1$ to $R^8$ in formula (2) is represented by —$SiY^1Y^2Y^3$. Examples of $Y^1$, $Y^2$ and $Y^3$ include the same groups as the above-mentioned substituted or unsubstituted alkyl groups.

As a halogen atom, fluoride, chlorine, bromine and iodine are exemplified.

As unsymmetric anthracene compounds, compounds represented by formulas (2-1) to (2-3) are more preferable.

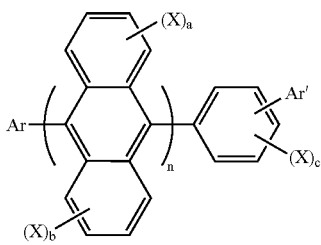

(2-1)

wherein Ar is a substituted or substituted condensed aromatic group having 10 to 50 nucleus carbon atoms, Ar' is a substituted or unsubstituted aryl group having 6 to 50 nucleus carbon atoms, X is a hydrogen atom, a substituted or unsubstituted aryl group having 6 to 50 nucleus carbon atoms, substituted or unsubstituted aromatic heterocyclic group having 5 to 50 nucleus carbon atoms, a substituted or unsubstituted arkyl group having 2 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arythio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group.

a, b and c are each an integer of 0 to 4 and n is an integer of 1 to 3.

Examples of the substituted or unsubstituted condensed aromatic group of Ar in formula (2-1) include 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 3-methyl-2-naphthyl, 4-methyl-1-naphthyl, and 4-methyl-1-anthryl groups.

Examples of the substituted or unsubstituted aryl group of Ar' in formula (2-1) include the above-mentioned examples and phenyl group.

Examples of the substituted or unsubstituted aryl, aromatic heterocyclic, alkyl, alkoxy, aralkyl, aryloxy, arylthio, alkoxycarbonyl and silyl group of X in formula (2-1) include the above-mentioned examples.

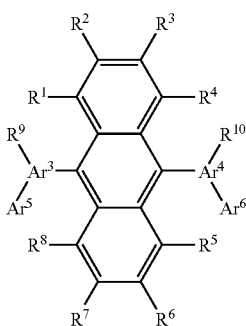

(2-2)

wherein $Ar^3$ and $Ar^4$ are independently a substituted or unsubstituted condensed aromatic group having 10 to 20 nucleus carbon atoms, $Ar^5$ and $Ar^6$ are independently a hydrogen atom or a substituted or unsubstituted aryl group with 6 to 50 nucleus carbon atoms, and $R^1$ to $R^{10}$ are independently a hydrogen atom or a substituted or unsubstituted aryl group having 6 to 50 nucleus carbon atoms, a substituted or unsubstituted aromatic hetrocyclic group having 5 to 50 nucleus carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group, provided that groups do not symmetrically bond to 9 and 10 positions of the central anthracene.

Examples of the substituted or unsubstituted condensed aromatic group of $Ar^3$ and $Ar^4$ in formula (2-2) include bivalent groups of the above-mentioned examples.

Examples of the substituted or unsubstituted aryl group of $Ar^5$ and $Ar^6$ in formula (2-2) include the above-mentioned examples.

Examples of the substituted or unsubstituted aryl, aromatic heterocyclic, alkyl, alkoxy, aralkyl, aryloxy, arylthio, alkoxycarbonyl and silyl groups of $R^1$ to $R^{10}$ in formula (2-2) include the above-mentioned examples.

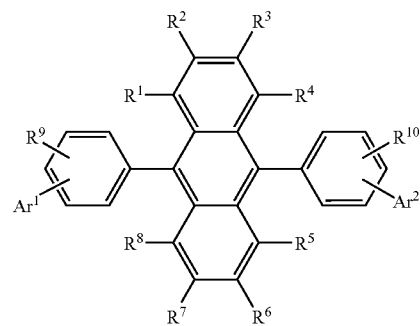

(2-3)

wherein $Ar^1$ and $Ar^2$ are independently a substituted or unsubstituted aryl group having 6 to 50 nucleus carbon atoms, and $R^1$ to $R^{10}$ are independently a hydrogen atom, a substituted or unsubstituted aryl group having 6 to 50 nucleus carbon atoms, a substituted or unsubstituted aromatic hetrocyclic group having 5 to 50 nucleus carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group.

Examples of the substituted or unsubstituted aryl group of $Ar^1$ and $Ar^2$ in formula (2-3) include the above-mentioned examples.

Examples of the substituted or unsubstituted aryl, aromatic heterocyclic, alkyl, alkoxy, aralkyl, aryloxy, arylthio, alkoxycarbonyl and silyl groups of $R^1$ to $R^{10}$ in formula (2-3) include the above-mentioned examples.

Examples of substituents for each of the above groups include halogen atoms, hydroxyl, nitro, cyano, alkyl, aryl, cycloalkyl, alkoxy, aromatic heterocyclic, aralkyl, aryloxy, arylthio, alkoxycarbonyl and carboxyl groups.

The above-mentioned unsymmetric anthracene compounds can be produced using a method described in Japanese Patent Application No. 2004-042696.

The thickness of a green emitting layer is preferably 2 to 50 nm, more preferably from 5 to 30 nm. When the thickness is as too thin as less than 5 nm, green emission may be too weak. When the thickness is more than 50 nm, green emission may be too strong to generate a white color.

A blue emitting layer is preferably a layer which emits light with a maximum wavelength of 400 to 500 nm and contains a host material and a blue dopant.

As the host material, the same materials used for a green emitting layer can be used. The above-mentioned unsymmetric anthracene compounds are preferred.

The blue dopant is not particularly limited, but is preferably at least one compound selected from styrylamines, amine-substituted styryl compounds, amine-substituted condensed aromatic rings and condensed-aromatic-ring containing compounds.

Examples of the styrylamines and amine-substituted styryl compounds are compounds represented by formulas (3-1) and (3-2), and examples of amine-substituted condensed aromatic rings and condensed-aromatic-ring containing compounds are compounds represented by formula (3-3).

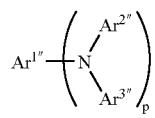

(3-1)

wherein $Ar^{1\prime\prime}$, $Ar^{2\prime\prime}$ and $Ar^{3\prime\prime}$ are independently a substituted or unsubstituted aromatic group having 6 to 40 carbon atoms and at least one thereof contains a styryl group; and p is an integer of 1 to 3.

Examples of the substituted and unsubstituted aromatic group include the above-mentioned groups.

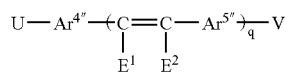

(3-2)

wherein $Ar^{4\prime\prime}$ and $Ar^{5\prime\prime}$ are independently a substituted or unsubstituted arylene group having 6 to 30 carbon atoms, $E^1$ and $E^2$ are independently a substituted or unsubstituted aryl or alkyl group having 6 to 30 carbon atoms, a hydrogen atom or a cyano group; q is an integer of 1 to 3; and U and/or V is a substituent containing an amino group and the amino group is preferably an arylamino group.

Examples of the aryl and alkyl groups include the above-mentioned groups and examples of the arylene group include groups obtained by removing one hydrogen atom from the above aryl groups.

(3-3)

wherein A is a substituted or unsubstituted alkyl or alkoxy group having 1 to 16 carbon atoms, a substituted or unsubstituted aryl group having 6 to 30 carbon atoms, a substituted or unsubstituted alkylamino group having 6 to 30 carbon atoms or a substituted or unsubstituted arylamino group having 6 to 30 carbon atoms; B is a condensed aromatic group having 10 to 40 carbon atoms; and r is an integer of 1 to 4.

Examples of the substituted or unsubstituted alkyl and the other groups include the above-mentioned groups.

The above-mentioned blue dopant can be produced by the method shown in WO02/20459.

The content of a blue dopant in a blue emitting layer is preferably 0.5 to 25 wt %, more preferably 2.5 to 5 wt %.

The thickness of a blue emitting layer is preferably from 2 to 50 nm, more preferably from 5 to 30 nm. If the thickness is as too thin as less than 2 nm, blue emission may be too week. If the thickness is more than 50 nm, blue emission may be too strong to generate a white color.

A red emitting layer is preferably a layer which emits light with a maximum wavelength of 570 to 700 nm, and contains a host material and a red dopant.

As the host material, the same materials used for a green emitting layer can be used. The above-mentioned unsymmetric anthracene compounds are preferred.

A red dopant is not particularly limited, but is a preferably compound containing a fluoranthene or perylene skeleton, and is more preferably a compound containing a plurality of fluoranthene skeletons. Examples thereof are as follows.

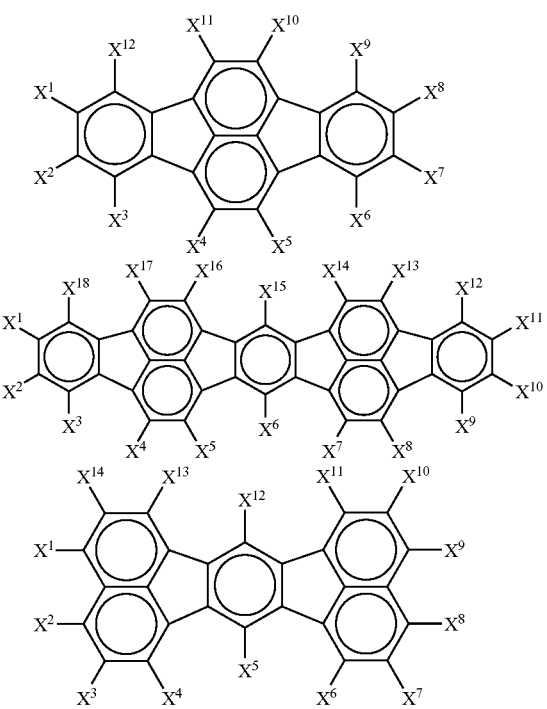

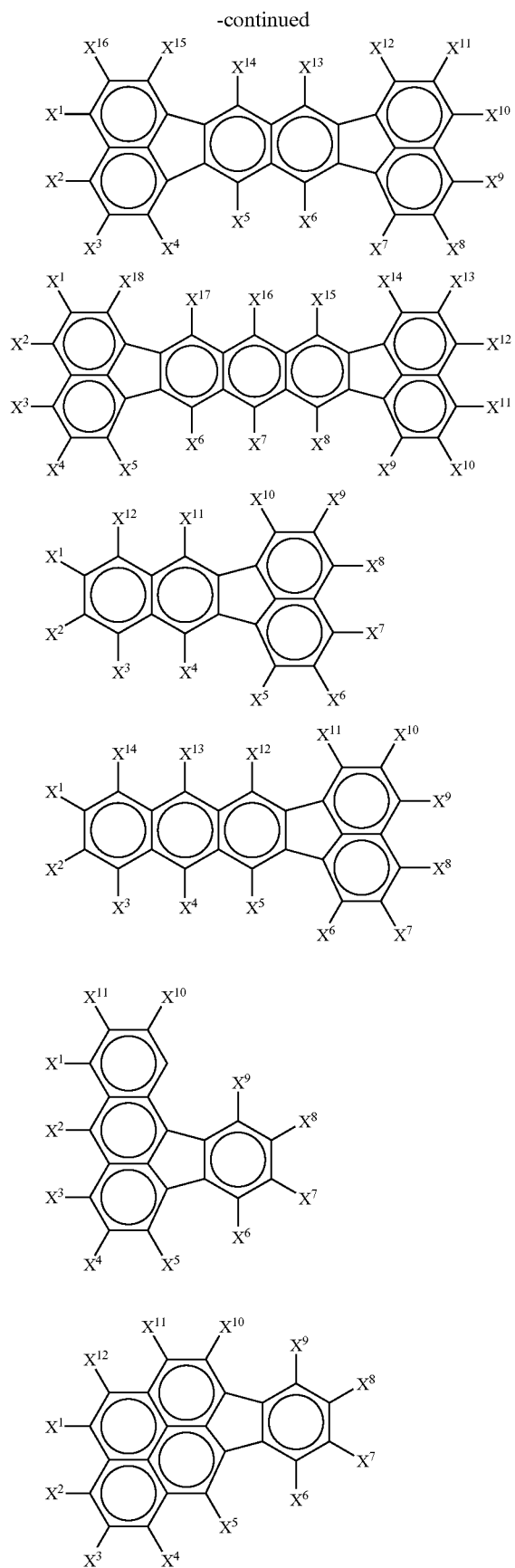
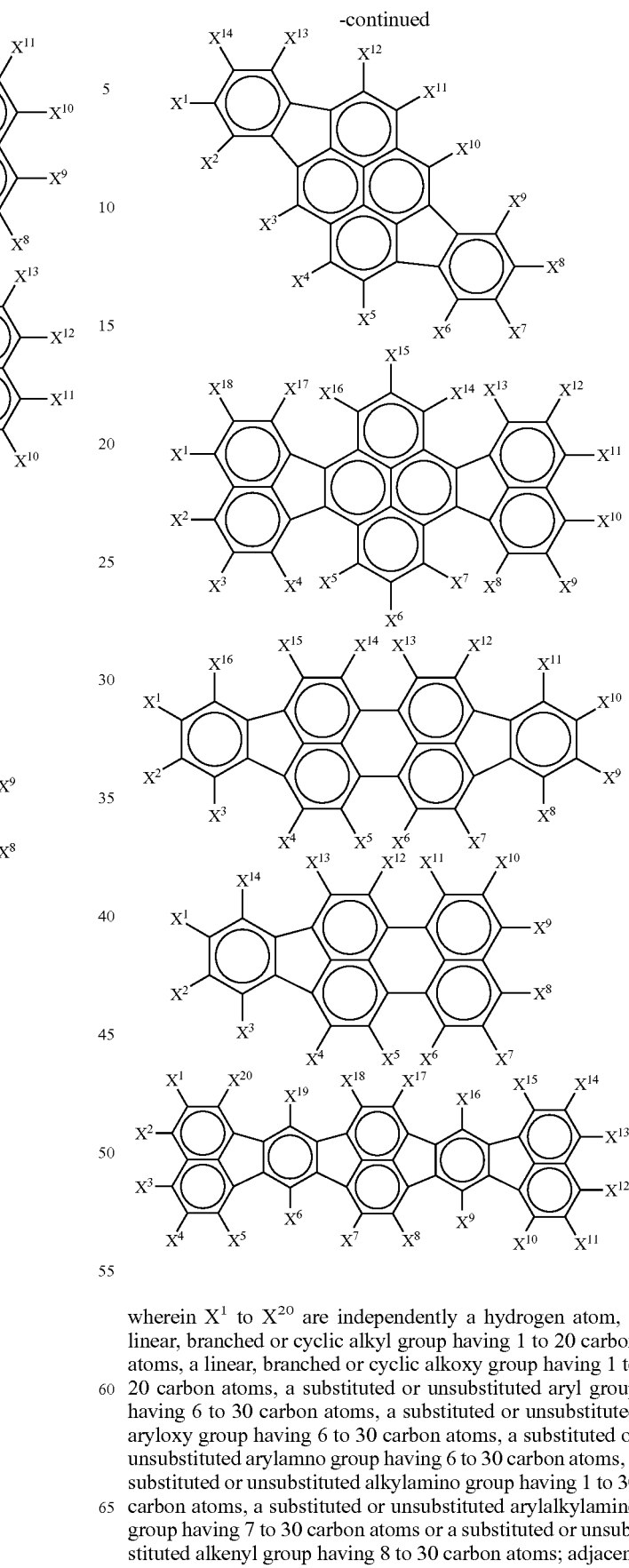

wherein $X^1$ to $X^{20}$ are independently a hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon atoms, a substituted or unsubstituted arylamno group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl group having 8 to 30 carbon atoms; adjacent substituents and $X^1$ to $X^{20}$ may be bonded to form a cyclic structure; and when adjacent substituents are aryl groups, the substituents may be the same.

Examples of the alkyl and other groups include the above-mentioned groups, and examples of the alkenyl group include the examples of alkyl group containing a double bond.

The compounds exemplified above preferably contain an amino or alkenyl group.

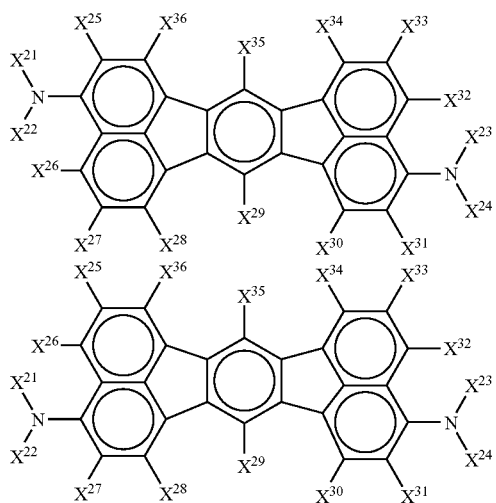

wherein $X^{21}$ to $X^{24}$ are independently an alkyl group having 1 to 20 carbon atoms or a substituted or unsubstituted aryl group having 6 to 30 carbon atoms; $X^{21}$ and $X^{22}$ and/or $X^{23}$ and $X^{24}$ may be bonded via a carbon-carbon bond, —O— or —S—; $X^{25}$ to $X^{36}$ are a hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon atoms, a substituted or unsubstituted arylamno group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl group having 8 to 30 carbon atoms; adjacent substituents and $X^{25}$ to $X^{36}$ may be bonded to form a cyclic structure; and at least one of the substituents $X^{25}$ to $X^{36}$ in each of the formulas preferably contain an amine or alkenyl group.

Examples of the alkyl and other groups include the above-mentioned groups and examples of the alkenyl group include the examples of alkyl group containing a double bond.

Fluorescent compounds containing a fluoranthene skeleton as mentioned above preferably contain an electron-donating group for high efficiency and long lifetime. Preferred electron-donating group is a substituted or unsubstituted arylamino group. The fluorescent compounds containing a fluoranthen skeleton preferably have 5 or more condensed rings and particularly preferably 6 or more condensed rings. The reason is that the fluorescent compounds emit fluorescence with a peak wavelength of 540 to 700 nm, and overlapping of emission from blue and green emitting materials and fluorescent compounds generates a white color. The above-mentioned fluorescent compounds preferably contain a plurality of fluoranthen skeletons; they more preferably contain an electron-donating group and a fluoranthen or perylane skeleton and emit fluorescence with a peak wavelength of 540 to 700 nm.

The above-mentioned red dopant can be produced by the method shown in WO01/23497.

The content of a red dopant in a red emitting layer is preferably 0.25 to 25 wt %, more preferably 0.5 to 5 wt %.

The thickness of a red emitting layer is preferably from 2 to 50 nm, more preferably from 5 to 30 nm. If the thickness is less than 2 nm, red emission may be too week like the blue and green emitting layers. If the thickness is more than 50 nm, red emission may be too strong to generate a white color.

A green/red emitting layer is preferably a layer which emits light with a maximum wavelength of 500 to 700 nm, and contains a host material, a green dopant of an aromatic amine compound represented by formula (1) and a red dopant. Examples of the host material, green dopant and red dopant are the same as the above-mentioned compounds and the explanation is thus omitted. The host material is preferably the above-mentioned unsymmetric anthracene compounds like the blue and green emitting layers. When blue, green and red emitting layers each use the same host material, they can be easily formed.

The content of each dopant contained in a green/red emitting layer may be the same as in the case where only single dopant is contained in a layer.

The thickness of a green/red emitting layer is preferably from 5 to 50 nm, more preferably from 20 to 40 nm. If the thickness is less than 5 nm, the luminance intensity of a green or red component may be week. If the thickness is more than 50 nm, green or red emission may be extremely intensified not to generate a white color, depending on its thickness relative to a blue emitting layer.

Layers other than the emitting layers which constitute the white organic EL device of the invention will be explained below.

The white organic EL device of the invention is fabricated on a transparent substrate. The transparent substrate is a substrate for supporting the organic EL device, and is preferably a flat or smooth substrate having a transmittance of 50% or more to light rays within visible ranges of 400 to 700 nm. Specific examples thereof include a glass plate and a polymer plate. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic resin, polyethylene terephthalate, polyethersulfide, and polysulfone.

In the invention, when light is taken out from the opposite side of a supporting substrate (top emission type), a white organic EL device may be fabricated on an opaque supporting substrate.

In the white organic EL device of the invention, a hole-injecting layer, a hole-transporting layer, an organic semiconductor layer and the like can be arranged between an anode and an emitting layer. The hole injecting or transporting layer is a layer for helping the injection of holes into the emitting layer so as to transport holes to a light emitting region. The hole mobility thereof is large and the ionization energy thereof is usually as small as 5.5 eV or less. The hole-injecting layer is formed to control the energy level, for example, to reduce rapid energy level changes. Such a hole injecting or transporting layer is preferably made of a material which can transport holes to the emitting layer at a lower electric field intensity. The hole mobility thereof is preferably at least $10^{-6}$ cm$^2$/V·second when an electric field of, e.g., $10^4$ to $10^6$ V/cm is applied. The material for forming the hole injecting or transporting layer can be arbitrarily selected from materials which have been widely used as a hole transporting material in photoconductive materials and known materials used in a hole-injecting layer of organic EL devices.

Examples of materials for such a hole-injecting layer and a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712 and 47-25336, JP-A-54-53435, 54-110536 and 54-119925, and others), arylamine derivatives (see U.S. Pat. Nos. 3,567,450, 3,180,703, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. Nos. 3,717,462, JP-A-54-59143, 55-52063, 55-52064, 55-46760, 55-85495, 57-11350, 57-148749 and 2-311591, and others), stylbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), electroconductive oligomers (in particular thiophene oligomers) disclosed in JP-A-1-211399, porphyrin compounds (disclosed in JP-A-63-2956965 and others), aromatic tertiary amine compounds and styrylamine compounds (see U.S. Pat. No. 4,127,412, JP-A-53-27033, 54-58445, 54-149634, 54-64299, 55-79450, 55-144250, 56-119132, 61-295558, 61-98353 and 63-295695, and others), the aromatic tertiary amine compounds, 4,4'-bis(N-(1-naphthyl)-N-phenylamino) biphenyl, which has in the molecule thereof two condensed aromatic rings, disclosed in U.S. Pat. Nos. 5,061,569, and 4,4',4"-tris(N-(3-methylphenyl)-N-phenylamino)triphenylamine, wherein three triphenylamine units are linked to each other in a star-burst form, disclosed in JP-A-4-308688. Inorganic compounds such as p-type Si and p-type SiC can also be used.

A hole injecting or transporting layer may be a single layer made of one or more out of the above-mentioned materials. A hole injecting or transporting layer may be formed by stacking hole injecting or transporting layers made of different compounds.

The thickness of the hole injecting or transporting layer is not particularly limited, and is preferably from 20 to 200 nm.

The organic semiconductor layer is a layer for helping the injection of holes or electrons into the emitting layer, and is preferably a layer having an electro conductivity of $10^{-10}$ S/cm or more. The material of such an organic semiconductor layer may be an electroconductive oligomer, such as a thiophene-containing oligomer or arylamine-containing oligomer disclosed in JP-A-8-193191, an electroconductive dendrimer such as an arylamine-containing dendrimer.

The thickness of the organic semiconductor layer is not particularly limited, and is preferably from 10 to 1,000 nm.

In the white organic EL device of the invention, an electron-injecting layer, an electron-transporting layer, an adhesion improving layer and the like can be arranged between a cathode and an emitting layer. The electron-injecting layer is a layer for helping the injection of electrons into the emitting layer, and has large electron mobility. The electron-injecting layer and electron-transporting layer are layers with a large electron mobility for controling the energy level, for example, reduceing rapid energy level changes. The adhesion improving layer is a layer made of a material particularly good in adhesion to the cathode among such electron-injecting layers.

The material used in the electron injecting or transporting layer is preferably a metal complex of 8-hydroxyquinoline or a derivative thereof.

Specific examples of the above-mentioned metal complex of 8-hydroxyquinoline or derivative include metal chelate oxynoid compounds containing a chelate of oxine (generally, 8-quinolinol or 8-hydroxyquinoline). For example, tris(8-quinolinol)aluminum(Alq) and so on can be used.

Examples of the oxadiazole derivative include electron-transferring compounds represented by the following general formulas.

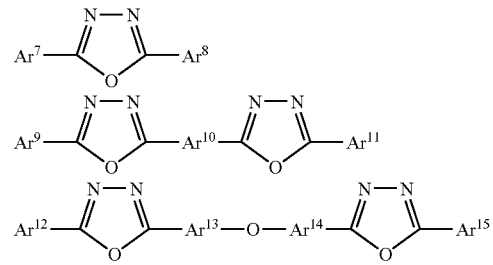

wherein $Ar^7$, $Ar^8$, $Ar^9$, $Ar^{11}$, $Ar^{12}$ and $Ar^{15}$ each represent a substituted or unsubstituted aryl group and may be the same as or different from each other, and $Ar^{10}$, $Ar^{13}$ and $Ar^{14}$ represent substituted or unsubstituted arylene groups and may be the same as or different from each other.

Examples of the aryl group include phenyl, biphenyl, anthranyl, perylenyl, and pyrenyl groups. Examples of the arylene group include phenylene, naphthylene, biphenylene, anthranylene, perylenylene, and pyrenylene groups. Examples of the substituent include alkyl groups with 1 to 10 carbon atoms, alkoxy groups with 1 to 10 carbon atoms, and a cyano group. The electron transferring compounds are preferably ones having capability of forming a thin film.

Specific examples of the electron transferring compounds include the following.

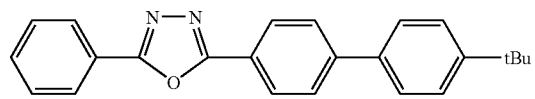

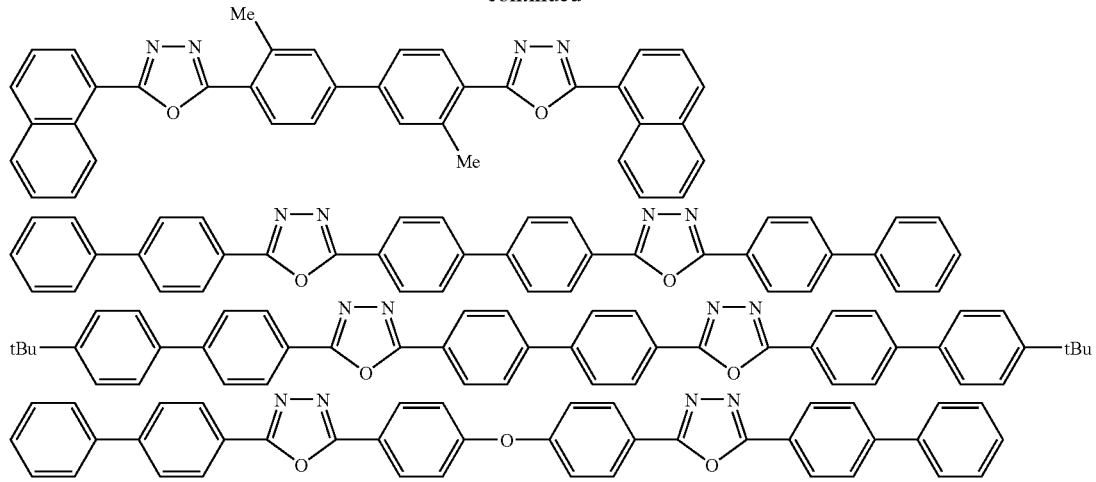

Me is methyl and Bu is butyl.

The following materials can be used for an electron-injecting layer and an electron-transporting layer. Nitrogen-containing heterocyclic derivatives represented by the following formula

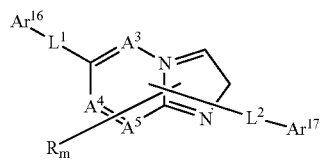

wherein $A^3$ to $A^5$ are independently a nitrogen atom or a carbon atom; $Ar^{16}$ is a substituted or unsubstituted aryl group having 6 to 60 nucleus carbon atoms or a substituted or unsubstituted heteroaryl group having 3 to 60 nucleus carbon atoms; $Ar^{17}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, or a substituted or unsubstituted alkoxy group having 1 to 20 carbon atoms; provided that one of $Ar^{16}$ and $Ar^{17}$ is a substituted or unsubstituted condensed ring having 10 to 60 nucleus carbon atoms or a substituted or unsubstituted monohetero condensed ring having 3 to 60 nucleus carbon atoms;

$L^1$ and $L^2$ are independently a single bond, a substituted or unsubstituted arylane group having 6 to 60 nucleus carbon atoms, a substituted or unsubstituted heteroarylane group having 3 to 60 nucleus carbon atoms or a substituted or unsubstituted fluorenylene group;

R is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms or a substituted or unsubstituted alkoxy group having 1 to 20 carbon atoms;

m is an integer of 0 to 5 and when m is 2 or more, Rs may be the same or different; and adjacent Rs may be bonded together to form a carbocyclic aliphatic ring or a carbocyclic aromatic ring.

Examples of the alkyl group and other groups include the above-mentioned groups.

Nitrogen-containing heterocyclic derivatives represented by the following formula

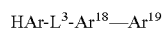

wherein HAr is a nitrogen-containing heterocyclic ring with 3 to 40 carbon atoms which may have a substituent; $L^3$ is a single bond, an arylane group with 6 to 60 carbon atoms which may have a substituent, a heteroarylane group with 3 to 60 carbon atoms which may have a substituent or a fluorenylene group which may have a substituent;

$Ar^{18}$ is a bivalent aromatic hydrocarbon group with 6 to 60 carbon atoms which may have a substituent; and $Ar^{19}$ is an aryl group with 6 to 60 carbon atoms which may have a substituent or a heteroaryl group with 3 to 60 carbon atoms which may have a substituent.

Examples of the aryle group and other groups include the above-mentioned groups.

An EL device using a silacyclopentadiene derivative represented by the following formula, disclosed in JP-A-09-087616

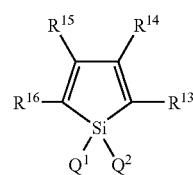

wherein $Q^1$ and $Q^2$ are each a saturated or unsaturated hydrocarbon group with 1 to 6 carbon atoms, an alkoxy group, an alkenyloxy group, an alkynyloxy group, a hydroxyl group, a substituted or unsubstituted aryl group, or a substituted or unsubstituted heterocyclic group, or $Q^1$ or $Q^2$ are bonded to each other to form a saturated or unsaturated ring; $R^{13}$ to $R^{16}$ are each a hydrogen atom, a halogen atom, a substituted or unsubstituted alkyl group with 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoil group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group or a cyano group, or a structure formed by condensing adjacent substituted or unsubstituted rings.

Borane derivatives represented by the following formula, disclosed in JP-A1-2000-040586

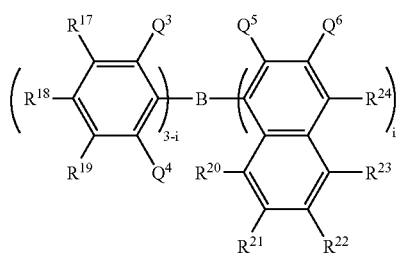

wherein $R^{17}$ to $R^{24}$ and $Q^6$ are each a hydrogen atom, a saturated or unsaturated hydrocarbon group, an aromatic group, a heterocyclic group, a substituted amino group, a substituted boryl group, an alkoxy group or an aryloxy group; $Q^3$, $Q^4$ and $Q^5$ are each a saturated or unsaturated hydrocarbon group, an aromatic group, a heterocyclic group, a substituted amino group, an alkoxy group or an aryloxy group; the substituent of $Q^5$ and $Q^6$ may be bonded to each other to form condensed rings; i is an integer of 1 to 3, and $Q^5$s may be different from each other when i is 2 or more; provided that excluded are the compounds where i is 1, $Q^3$, $Q^4$ and $R^{18}$ are a methyl group and $R^{24}$ is a hydrogen atom or substituted boryl group, and the compounds where i is 3 and $Q^5$ is a methyl group.

Compounds represented by the following formula, disclosed in JP-A-10-088121

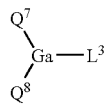

wherein $Q^7$ and $Q^8$ are independently a ligand represented by the following formula (I); and $L^3$ is a halogen atom, a substituted or unsubstituted alkyl group, a substituted or unsubstituted cycloalkyl group, a substituted or unsubstituted aryl group, a substituted or unsubstituted heterocyclic group, —$OR^{25}$ wherein $R^{25}$ is a hydrogen atom, a substituted or unsubstituted alkyl group, a substituted or unsubstituted cycloalkyl group, a substituted or unsubstituted aryl group, a substituted or unsubstituted heterocyclic group, or —O—Ga-$Q^9(Q^{10})$ wherein $Q^9$ and $Q^{10}$ are the same legand as $Q^7$ and $Q^8$.

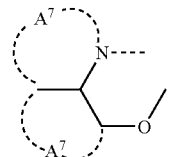

wherein rings $A^6$ and $A^7$ form a substituted or unsubstituted structure where 6-membered aryl rings are condensed.

The metal complexes have the strong nature of an n-type semiconductor and large ability of injecting electrons. Further the energy generated at the time of forming a complex is small and a metal is then strongly bonded to ligands in the complex formed with a large fluorescent quantum efficiency.

Specific examples of the rings $A^6$ and $A^7$ which form the ligands of the above formula include halogen atoms such as chlorine, bromine, iodine and fluorine; substituted or unsubstituted alkyl groups such as methyl, ethyl, propyl, butyl, sec-butyl, tert-butyl, pentyl, hexyl, heptyl, octyl, stearyl and trichloromethyl; substituted or unsubstituted aryl groups such as phenyl, naphthyl, 3-methylphenyl, 3-methoxyphenyl, 3-fluorophenyl, 3-trichloromethylphenyl, 3-trifluoromethylphenyl and 3-nitrophenyl; substituted or unsubstituted alkoxy groups such as methoxy, n-butoxy, tert-butoxy, trichloromethoxy, trifluoroethoxy, pentafluoropropoxy, 2,2,3,3-tetrafluoropropoxy, 1,1,1,3,3,3-hexafluoro-2-propoxy and 6-(perfluoroethyl)hexyloxy; substituted or unsubstituted aryloxy groups such as phenoxy, p-nitrophenoxy, p-tert-butylphenoxy, 3-fluorophenoxy, pentafluorophenyl and 3-trifluoromethylphenoxy; substituted or unsubstituted alkylthio groups such as methythio, ethylthio, tert-butylthio, hexylthio, octylthio and trifruoromethyltio; substituted or unsubstituted arylthio groups such as phenylthio, p-nitrophenylthio, p-tert-butylphenylthio, 3-fluorophenylthio, pentafluorophenylthio and 3-trifluoromethylphenylthio; a cyano group; a nitro group, an amino group; mono or di-substituted amino groups such as methylamino, dimethylamino, ethylamino, diethylamino, dipropylamino, dibutylamino and diphenylamino; acylamino groups such as bis(acetoxymethyl)amino, bis(acetoxyethyl)amino, bis(acetoxypropyl)amino and bis(acetoxybutyl)amino; a hydroxy group; a siloxy group; an acyl group; carbamoyl groups such as methylcarbamoyl, dimethylcarbamoyl, ethylcarbamoyl, diethylcarbamoyl, propylcarbamoyl, butylcarbamoyl and phenylcarbamoyl; a carboxylic group; a sulfonic acid group; an imido group; cycloalkyl groups such as cyclopentyl and cyclohexyl; aryl groups such as phenyl, naphthyl, biphenyl, anthranyl, phenanthryl, fluorenyl and pyrenyl; and heterocyclic groups such as pyridinyl, pyrazinyl, pyrimidinyl, pryidazinyl, triazinyl, indolinyl, quinolinyl, acridinyl, pyrrolidinyl, dioxanyl, piperidinyl, morpholidinyl, piperazinyl, triathinyl, carbazolyl, furanyl, thiophenyl, oxazolyl, oxadiazolyl, benzooxazolyl, thiazolyl, thiadiazolyl, benzothiazolyl, triazolyl, imidazolyl, benzoimidazolyl and puranyl. Moreover the above-mentioned substituents may be bonded to each other to form a six-membered aryl or heterocyclic ring.

An electron-injecting layer or an electron-transporting layer may be a single layer made of one or two or more of the above-mentioned materials, or multiple layers of electron-injecting layers or electron-transporting layers made of different compounds.

The thickness of the electron-injecting layer or the electron-transporting layer is not particularly limited, and is preferably 1 to 100 nm.

The white organic EL device of the invention may contain a reducing dopant in an electron transporting region or an interface region between a cathode and an organic layer. The reducing dopant here is defined as a substance which can reduce electron transporting compounds. Various substances having a certain reducibility can be used. The following can be preferably used: at least one substance selected from alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals.

Preferable examples of the reducing dopant are at least one alkali metal selected from Na (work function: 2.36 eV), K (work function: 2.28 eV), Rb (work function: 2.16 eV) and Cs (work function: 1.95 eV) or at least one alkaline earth metal selected from Ca (work function: 2.9 eV), Sr (work function: 2.0 to 2.5 eV) and Ba (work function: 2.52 eV). More preferred are ones having a work function of 2.9 eV or less. Among these, a more preferable reducing dopant is at least one alkali metal selected from K, Rb and Cs, even more preferably Rb and Cs and the most preferably Cs. These alkali metals have a particularly high reducing ability, and therefore adding a relatively small amount thereof into an electron injecting region enhances the luminance and lifetime of the organic EL device. As a reducing dopant having a work function of 2.9 eV or less, combinations of two or more of these alkali metals are preferable. Combinations with Cs, for example, Cs and Na, Cs and K, Cs and Rb or Cs, Na and K are particularly preferable. The combination with Cs efficiently exhibits a reducing ability and the addition thereof into an electron injecting region enhances the luminance and the lifetime of the organic EL device.

In the invention, an electron-injecting layer or an electron-transporting layer which is formed of an insulator or a semiconductor may further be provided between a cathode and an organic layer. By providing the layers, current leakage can be effectively prevented to improve the injection of electrons. The inorganic compound of insulator or semiconductor is preferably a microcrystalline or amorphous insulating thin film. If an electron-transporting layer is formed of the insulating thin film, a more uniform thin film can be formed to reduce pixel defects such as dark spots.

As the insulator, at least one metal compound selected from alkali metal calcogenides, alkaline earth metal calcogenides, halides of alkali metals and halides of alkaline earth metals can be preferably used. If an electron-injecting layer is formed of these compounds, the injection of electrons can be preferably improved. Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Examples of the semiconductor include oxides, nitrides or oxynitrides containing at least one element selected from Ba, Ca, Sr, Yb, Al, Ga, In, Li, Na, Cd, Mg, Si, Ta, Sb and Zn, and combinations of two or more thereof.

The white organic EL device of the invention preferably contains an oxidant in an emitting layer or an organic layer between an emitting layer and an anode. Preferable oxidants are electron attractors or electron acceptors. Examples thereof include Lewis acids, various quinone derivatives, dicyanoquinodimethane derivatives, and salts of aromatic amines and Lewis acids. Examples of Lewis acids include iron chloride, antimony chloride and aluminum chloride.

The white organic EL device of the invention preferably contains a reducing agent in an emitting layer or an organic layer between an emitting layer and an anode. Preferable reducing agents are alkali metals, alkaline earth metals, oxides of alkali metals, oxides of alkaline earth metals, oxides of rare earth metals, halides of alkali metals, halides of alkaline earth metals, halides of rare earth metals, and complexes formed of alkali metals and aromatic compounds. Particularly preferred alkali metals are Cs, Li, Na and K.

The white organic EL device of the invention may include an inorganic compound layer(s) in contact with an anode and/or a cathode. The inorganic compound layer functions as an adhesion-improving layer. Preferable inorganic compounds used for the inorganic compound layer are oxides of alkali metals, oxides of alkaline earth metals, oxides of rare earth metals, halides of alkali metals, halides of alkaline earth metals, halides of rare earth metals and various oxides, nitrides and oxynitrides such as $SiO_x$, $AlO_x$, $SiN_x$, SiON, AlON, $GeO_x$, $LiO_x$, LiON, $TiO_x$, TiON, $TaO_x$, TaON, $Ta_{n_x}$ and C. As a component of a layer in contact with an anode, $SiO_x$, $AlO_x$, $SiN_x$, SiON, AlON, $GeO_x$ and C are preferred since a stable injecting interface layer is formed. As a component of a layer in contact with a cathode, Lif, $MgF_2$, $CaF_2$ and $NaF_2$ are preferred.

The thickness of the inorganic compound layer is not limited, and is preferably 0.1 nm to 100 nm.

A method of forming organic and inorganic layers including an emitting layer is not limited. Known methods such as vacuum deposition, spin coating, casting and LB technique can be applied. Since the properties of an organic EL device obtained are constant and the fabrication time can be shortened, an electron-injecting layer and an emitting layer are preferably formed by the same method; for example, when an electron-injecting layer is formed by vacuum deposition, an emitting layer is preferably formed also by vacuum deposition.

For an anode, metals, alloys, electric conductive compounds or mixtures thereof which have a large work function (for example, 4.0 eV or more) are preferably used. Specifically indium tin oxide (ITO), indium zinc oxide, tin, zinc oxide, gold, platinum and palladium and combinations of two or more thereof can be used.

The thickness of an anode is not particularly limited, and is preferably 10 to 1,000 nm and more preferably 10 to 200 nm.

For a cathode, metals, alloys, electric conductive compounds or mixtures thereof which have a small work function (for example, less than 4.0 eV) are preferably used. Specifically magnesium, aluminum, indium, lithium, sodium and silver and combinations of two or more thereof can be used.

The thickness of a cathode is not particularly limited, and is preferably 10 to 1,000 nm and more preferably 10 to 200 nm.

At least one of an anode or a cathode preferably has a light transmittance of 10% or more in order to effectively take out light emitted from an emitting layer to the outside.

The electrodes can be formed by vacuum deposition, sputtering, ion plating, electron beam deposition, CVD, MOCVD, plasma CVD and so on.

EXAMPLES

Examples of the invention will be described below, but the invention is not limited to these examples.

Test Example (Ionization Potential Measurement)

An ionization potential (IP) was measured as follows. The powder dopant GD1 (0.3 g) shown below was uniformly spreaded in a circular shape with a diameter of 3 mm on a square slide with a side length of 1 cm so as to cover the surface of slide. The resultant was set on a sample holder of an airglow electron spectroscopy device AC-1 (manufactured by RIKEN KEIKI CO., LTD.) to measure its ionization potential. As a result, the ionization potential was 5.5 eV and the affinity (Af) was 3.0 eV because the energy gap (Eg) determined with an optical absorption was 2.5 eV.

GD2 (coumarin 5) of an ordinary green dopant was similarly measured. As a result, the ionization potential thereof was 5.3 eV, Eg was 2.6 eV and the affinity was 2.7 eV.

Furthermore, a blue dopant (BD1), red dopant (RD1) and unsymmetric anthrathene compound (BH1) were similarly measured for ionization potential, Eg and affinity. The results are shown in Table 1.

GD1

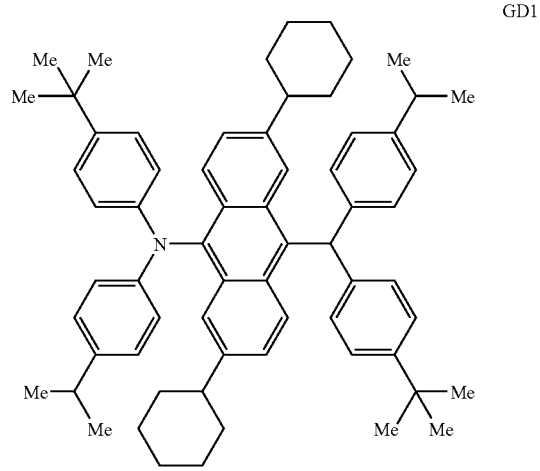

GD2

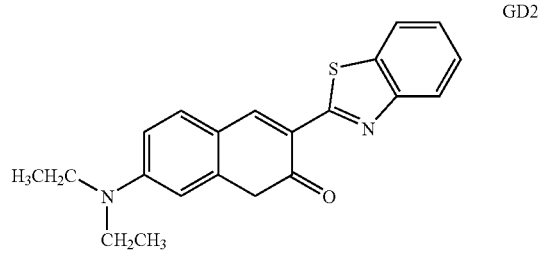

BD1

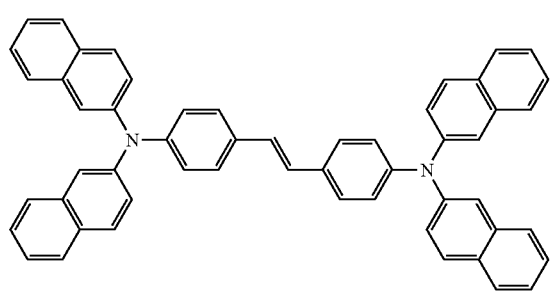

RD1

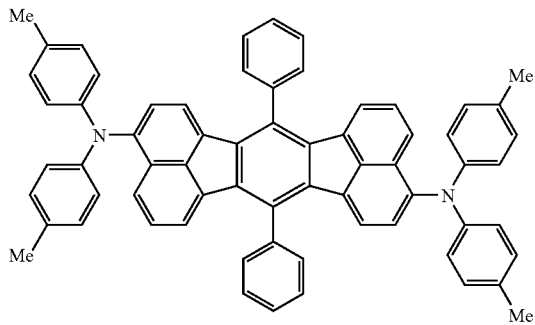

BH1

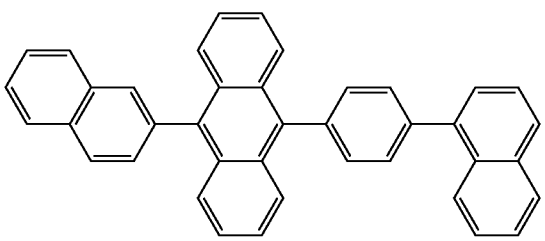

TABLE 1

|     | Ip(eV) | Eg(eV) | Af(eV) |
| --- | --- | --- | --- |
| BH1 | 5.8 | 3.0 | 2.8 |
| BD1 | 5.4 | 2.9 | 2.5 |
| GD1 | 5.5 | 2.5 | 3.0 |
| RD1 | 5.2 | 2.0 | 3.2 |
| GD2 | 5.3 | 2.6 | 2.7 |

Example 1

A grass substrate of 25 mm by 75 mm by 1.1 mm with an ITO transparent electrode (GEOMATEC CO., LTD.) was subjected to ultrasonic cleaning with isopropyl alcohol for 5 minutes, and cleaned with ultraviolet rays and ozone for 30 minutes. The resultant substrate was mounted on a substrate holder in a vacuum deposition device. First, the following compound (H1) was formed in a thickness of 60 nm so as to cover the surface of the transparence electrode on which transparence electrode lines were formed. (The film is referred to as HI film hereinafter.) This HI film functioned as a hole-injecting layer.

After forming the HI film, the following compound (HT) was formed in a thickness of 20 nm. (The film is referred to as HT film hereinafter.) This HT film functioned as a hole-transporting layer. Following the formation of the HT film, BH1 and BD1 were deposited to a thickness of 10 nm at a weight ratio of 40:2 to form a blue emitting layer. Next, BH1 and GD1 were deposited to a thickness of 10 nm at a weight ratio of 40:3 to form a green emitting layer. BH1 and RD1 were deposited to a thickness of 20 nm at a weight ratio of 40:1 to form a red emitting layer thereon.

As an electron-transporting layer, a 20 nm thick tris(8-quinolinol)aluminum film (Alq film) was formed thereon. Thereafter, LiF was deposited in a thickness of 1 nm as an electron-injecting layer and Al was deposited in a thickness of 150 nm as a cathode, thereby fabricating an organic EL device.

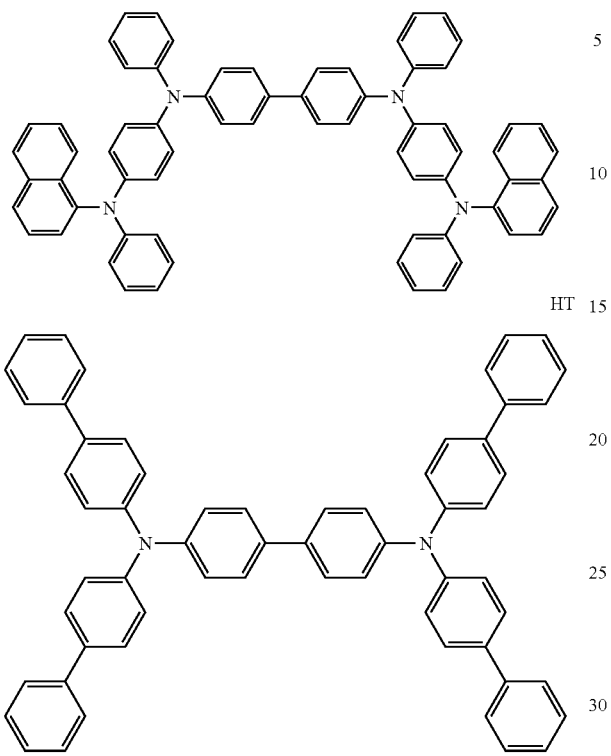

When applying current to the device at a current density of 10 mA/cm², a direct voltage was 6.8 V and white emission with a luminance of 1,140 cd/m² and a luminous efficiency of 11.4 cd/A was obtained. The chromaticity coordinates, CIE1931 were (x, y)=(0.283, 0.338), which confirmed white emission. When driven by a constant current at an initial luminance of 5,000 cd/m², a half life, a necessary time for luminance to be reduced by half, was excellently 980 hours.

Comparative Example 1

A device was fabricated in the same way as in Example 1 except that a dopant of a green emitting layer was changed from GD1 to GD2. That is, after stacking a blue emitting layer in a thickness of 10 nm like in Example 1, BH1 and GD2 were deposited to 10 nm at a weight ratio of 40:3 as a green emitting layer. Thereafter, layers were deposited in the same way as in Example 1 to fabricate a device.

When applying current to the device at a current density of 10 mA/cm², the direct voltage was 7.8 V and white emission with a luminance of 850 cd/m² and a luminous efficiency of 8.5 cd/A was obtained. The chromaticity coordinates, CIE1931 were (x, y)=(0.269, 0.353), which confirmed white emission. When driven by a constant current at an initial luminance of 5,000 cd/m², a half life, a necessary time for luminance to be reduced by half, was 350 hours, which was shorter than in Example 1.

Example 2

Blue Emitting Layer and Green/Red Emitting Layer (Blue/Blue-Green-Mixture Emitting Layers))

The same procedures as in Example 1 were repeated until a blue emitting layer was formed. Next, BH1, GD1 and RD1 were deposited to a thickness of 30 nm at a weight ratio of 40:3:1 as a green/red emitting layer. An electron-transporting layer and subsequent layers were deposited in the same way as in Example 1.

Table 2 shows the voltage, luminance and chromaticity when applying current to the device at a current density of 10 mA/cm² and the half life of luminance under constant current driving at an initial luminance of 5,000 cd/m².

Example 3

Blue Emitting Layer, Red Emitting Layer and Green Emitting Layer

The same procedures as in Example 1 were repeated until a blue emitting layer was formed. Next, a red emitting layer was deposited to 10 nm and a green emitting layer was deposited to 20 nm in the same condition as in Example 1. An electron-transporting layer and subsequent layers were deposited in the same way as in Example 1.

Table 2 shows the voltage, luminance and chromaticity when applying current to the device at a current density of 10 mA/cm² and the half life of luminance under constant current driving at an initial luminance of 5,000 cd/m².

TABLE 2

| | Voltage (V) | Luminance (cd/m²) | Chromaticity CIEx | CIEy | Half life of luminance (hour) (Initial luminance 5000 cd/m²) |
|---|---|---|---|---|---|
| Example 1 | 6.8 | 1140 | 0.283 | 0.338 | 980 |
| Comparative example 1 | 7.8 | 850 | 0.269 | 0.352 | 350 |
| Example 2 | 6.8 | 1085 | 0.339 | 0.294 | 1050 |
| Example 3 | 6.7 | 940 | 0.329 | 0.307 | 950 |

INDUSTRIAL APPLICABILITY

The white organic EL device of the invention can be used suitably for thin film optical source back lighting for LCD, lighting sources for vehicles and offices, and full color displays such as PDA, car navigation system and TV, and so on.

What is claimed is:
1. A white organic electroluminescent device comprising an emitting layer interposed between an anode and a cathode,
the emitting layer comprising a host material including a unsymmetric anthracene compound represented by formula (2-1), a blue dopant, a green dopant and a red dopant, and emitting blue light, green light and red light,
wherein the blue dopant is at least one compound selected from styryl amines, amine-substituted styryl compounds, amine-substituted condensed aromatic rings and condensed-aromatic-ring containing compounds;
the green dopant is an aromatic amine compound represented by formula (1);
the red dopant is a compound containing a fluoranthene or perylene skeleton;
the affinity levels of the blue dopant, the green dopant and the red dopant satisfying the relationship

$Af_b < Af_g < Af_r$, wherein $Af_g$ is 2.8 to 3.4 eV and
wherein $Af_b$ is the affinity level of the blue dopant, $Af_g$ is the affinity level of the green dopant and $Af_r$ is the affinity level of the red dopant; and formulae (1) and (2-1) are:

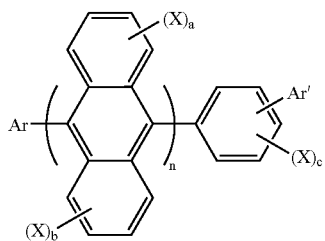

(2-1)

wherein Ar is a substituted or unsubstituted condensed aromatic group having 10 to 50 nucleus carbon atoms;

Ar' is a substituted or unsubstituted aryl group having 6 to 50 nucleus carbon atoms;

X is a hydrogen atom, a substituted or unsubstituted aryl group having 6 to 50 nucleus carbon atoms, substituted or unsubstituted aromatic heterocyclic group having 5 to 50 nucleus carbon atoms, a substituted or unsubstituted arkyl group having 2 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group; and a, b and c are each an integer of 0 to 4 and n is an integer of 1 to 3;

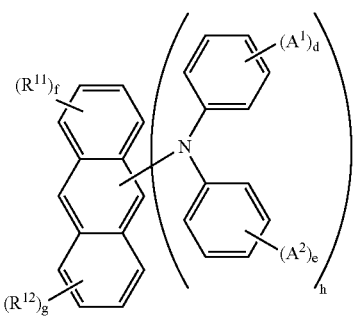

(1)

wherein $A^1$ to $A^2$ are independently a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted aryamino group having 5 to 50 nucleus carbon atoms, a substituted or unsubstituted alkylamino group having 1 to 10 carbon atoms or a halogen atom; d and e are independently an integer of 1 to 5; h is an integer of 1 to 9; when d and e are independently 2 or more, $A^1$s and $A^2$s may be the same or different and may be joined together to form a saturated or unsaturated ring; provided that compounds where both of $A^1$ and $A^2$ are hydrogen atoms are excluded;

$R^{11}$ is a substituted or unsubstituted secondary or tertiary alkyl group having 3 to 10 carbon atoms or a substituted or unsubstituted secondary or tertiary cycloalkyl group having 3 to 10 carbon atoms; f is an integer of 1 to 9; when f is 2 or more, $R^{11}$s may be the same or different; $R^{12}$ is a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted arylamino group having 5 to 50 nucleus carbon atoms, a substituted or unsubstituted alkylamino group having 1 to 10 carbon atoms, or a halogen atom; g is an integer of 0 to 8; when g is 2 or more, $R^{12}$s may be the same or different; and f+g+h is an integer of 2 to 10.

2. The white organic electroluminescent device according to claim 1, wherein the emitting layer has a three-layer structure of a blue emitting layer emitting blue light, a green emitting layer emitting green light and a red emitting layer emitting red light.

3. The white organic electroluminescent device according to claim 1, wherein the emitting layer has a two-layer structure of a blue emitting layer emitting blue light, and a green/red emitting layer emitting green light and red light.

4. The white organic electroluminescent device according to claim 1. wherein the ionization potential of the green dopant is equal to or larger than the ionization potential of the blue dopant.

5. A white organic electroluminescent device comprising in sequence an anode, a blue emitting layer comprising a host material including an unsymmetric anthracene compound represented by formula (2-1) and a blue dopant, a green emitting layer comprising a host material including an unsymmetric anthracene compound represented by formula (2-1) and a green dopant, a red emitting layer comprising a host material including an unsymmetric anthracene compound represented by formula (2-1) and a red dopant, and a cathode, wherein the blue dopant is at least one compound selected from styryl amines, amine-substituted styryl compounds, amine-substituted condensed aromatic rings and condensed-aromatic-ring containing compounds;

the green dopant is an aromatic amine compound represented by formula (1);

the red dopant is a compound containing a fluoranthene or perylene skeleton;

the affinity levels of the blue dopant and the green dopant satisfying the relationship $Af_b < Af_g$, wherein $Af_g$ is 2.8 to 3.4 eV and wherein $Af_b$ is the affinity level of the blue dopant and $Af_g$ is the affinity level of the green dopant;

the ionization potential of a green dopant forming the green emitting layer being equal to or larger than the ionization potential of a blue dopant forming the blue emitting layer; and formulae (1) and (2-1) are:

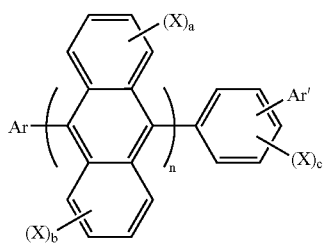

(2-1)

wherein Ar is a substituted or unsubstituted condensed aromatic group having 10 to 50 nucleus carbon atoms;
Ar' is a substituted or unsubstituted aryl group having 6 to 50 nucleus carbon atoms;
X is a hydrogen atom, a substituted or unsubstituted aryl group having 6 to 50 nucleus carbon atoms, substituted or unsubstituted aromatic heterocyclic group having 5 to 50 nucleus carbon atoms, a substituted or unsubstituted arkyl group having 2 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substitute or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group; and
a, b, and c are each an integer of 0 to 4 and n is an integer of 1 to 3;

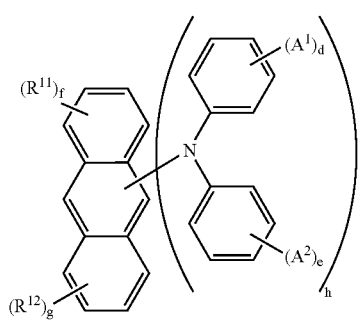

(1)

wherein $A^1$ to $A^2$ are independently a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted aryamino group having 5 to 50 nucleus carbon atoms, a substituted or unsubstituted alkylamino group having 1 to 10 carbon atoms or a halogen atom; d and e are independently an integer of 1 to 5; h is an integer of 1 to 9; when d and e are independently 2 or more, $A^1$s and $A^2$s may be the same or different and may be joined together to form a saturated or unsaturated ring; provided that compounds where both of $A^1$ and $A^2$ are hydrogen atoms are excluded;
$R^{11}$ is a substituted or unsubstituted secondary or tertiary alkyl group having 3 to 10 carbon atoms or a substituted or unsubstituted secondary or tertiary cycloalkyl group having 3 to 10 carbon atoms; f is an integer of 1 to 9; when f is 2 or more, $R^{11}$s may be the same or different; $R^{12}$ is a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted arylamino group having 5 to 50 nucleus carbon atoms, a substituted or unsubstituted alkylamino group having 1 to 10 carbon atoms, or a halogen atom; g is an integer of 0 to 8; when g is 2 or more, $R^{12}$s may be the same or different; and
f+g+h is an integer of 2 to 10.

6. A white organic electroluminescent device comprising in sequence an anode, a blue emitting layer comprising a host material including an unsymmetric anthracene compound represented by formula (2-1) and a blue dopant, a red emitting layer comprising a host material including an unsymmetric anthracene compound represented by formula (2-1) and a red dopant, a green emitting layer comprising a host material including an unsymmetric anthracene compound represented by formula (2-1) and a green dopant, and a cathode,
wherein the blue dopant is at least one compound selected from styryl amines, amine-substituted styryl compounds, amine-substituted condensed aromatic rings and condensed-aromatic-ring containing compounds;
the green dopant is an aromatic amine compound represented by formula (1);
the red dopant is a compound containing a fluoranthene or perylene skeleton;
the affinity levels of the green dopant and the red dopant satisfying the relationship $Af_g < Af_r$, wherein $Af_g$ is 2.8 to 3.4 eV and
wherein $Af_g$ is the affinity level of the green dopant and $Af_r$ is the affinity level of the red dopant;
the ionization potential of a green dopant forming the green emitting layer being equal to larger than the ionization potential of a blue dopant forming the blue emitting layer; and
formulae (1) and (2-1) are:

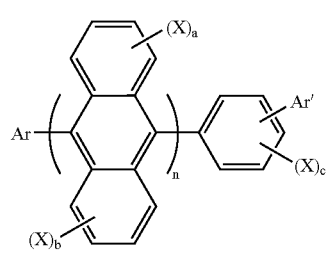

(2-1)

wherein Ar is a substituted or unsubstituted condensed aromatic group having 10 to 50 nucleus carbon atoms;

Ar' is a substituted or unsubstituted aryl group having 6 to 50 nucleus carbon atoms;

X is a hydrogen atom, a substituted or unsubstituted aryl group having 6 to 50 nucleus carbon atoms, substituted or unsubstituted aromatic heterocyclic group having 5 to 50 nucleus carbon atoms, a substituted or unsubstituted arkyl group having 2 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus carbon atoms, a substituted or unsubstituted arylthio group having 5 to 50 nucleus carbon atoms, a substituted or unsubstituted alkoxycarbonyl group having 2 to 50 carbon atoms, a substituted or unsubstituted silyl group having 1 to 50 carbon atoms, a carboxyl group, a halogen atom, a cyano group, a nitro group or a hydroxyl group; and a, b and c are each an integer of 0 to 4 and n is an integer of 1 to 3;

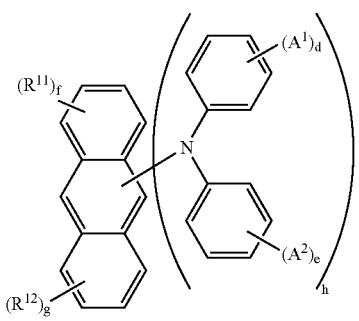

(1)

wherein $A^1$ to $A^2$ are independently a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted aryamino group having 5 to 50 nucleus carbon atoms, a substituted or unsubstituted alkylamino group having 1 to 10 carbon atoms or a halogen atom; d and e are independently an integer of 1 to 5; h is an integer of 1 to 9; when d and e are independently 2 or more, $A^1$s and $A^2$s may be the same or different and may be joined together to form a saturated or unsaturated ring; provided that compounds where both of $A^1$ and $A^2$ are hydrogen atoms are excluded;

$R^{11}$ is a substituted or unsubstituted secondary or tertiary alkyl group having 3 to 10 carbon atoms or a substituted or unsubstituted secondary or tertiary cycloalkyl group having 3 to 10 carbon atoms; f is an integer of 1 to 9; when f is 2 or more, $R^{11}$s may be the same or different;

$R^{12}$ is a hydrogen atom, a substituted or unsubstituted alkyl group having 1 to 10 carbon atoms, a substituted or unsubstituted aryl group having 5 to 50 nucleus carbon atoms, a substituted or unsubstituted cycloalkyl group having 3 to 20 nucleus carbon atoms, a substituted or unsubstituted alkoxy group having 1 to 10 carbon atoms, a substituted or unsubstituted aryloxy group having 5 to 50 nucleus carbon atoms, a substituted or unsubstituted arylamino group having 5 to 50 nucleus carbon atoms, a substituted or unsubstituted alkylamino group having 1 to 10 carbon atoms, or a halogen atom; g is an integer of 0 to 8; when g is 2 or more, $R^{12}$s may be the same or different; and f+g+h is an integer of 2 to 10.

7. The white organic electroluminescent device according to claim 5, wherein the
affinity levels of the blue dopant, the green dopant and the red dopant satisfy the relationship $Af_b < Af_g < Af_r$, wherein $Af_g$ is 2.8 to 3.4 eV and
wherein $Af_b$ is the affinity level of the blue dopant, $Af_g$ is the affinity level of the green dopant and $Af_r$ is the affinity level of the red dopant.

8. The white organic electroluminescent device according to claim 6, wherein the
affinity levels of the blue dopant, the green dopant and the red dopant satisfy the relationship $Af_b < Af_g < Af_r$, wherein $Af_g$ is 2.8 to 3.4 eV and
wherein $Af_b$ is the affinity level of the blue dopant, $Af_g$ is the affinity level of the green dopant and $Af_r$ is the affinity level of the red dopant.

9. The white organic electroluminescent device according to claim 1, wherein the unsymmetric anthracene compound comprises only one anthracene ring.

* * * * *